United States Patent
Spodsberg

(10) Patent No.: US 8,771,993 B1
(45) Date of Patent: Jul. 8, 2014

(54) POLYPEPTIDES HAVING ENDOGLUCANSE ACTIVITY AND POLYNUCLEOTIDES ENCODING SAME

(71) Applicants: Novozymes A/S, Bagsvaerd (DK); Novozymes Inc., Davis, CA (US)

(72) Inventor: Nikolaj Spodsberg, Bagsvaerd (DK)

(73) Assignees: Novozymes A/S, Bagsvaerd (DK); Novozymes Inc., Davis, CA (US)

( * ) Notice: Subject to any disclaimer, the term of this patent is extended or adjusted under 35 U.S.C. 154(b) by 0 days.

(21) Appl. No.: 13/764,912

(22) Filed: Feb. 12, 2013

(51) Int. Cl.
C12N 9/42 (2006.01)

(52) U.S. Cl.
CPC ..................................... C12N 9/244 (2013.01)
USPC ............. 435/99; 435/200; 435/196; 435/189; 435/212; 435/219; 435/209; 435/100; 435/101; 435/105; 435/106; 435/132; 435/136; 435/148; 435/155; 435/161; 435/160; 435/166; 435/168

(58) Field of Classification Search
None
See application file for complete search history.

(56) References Cited

U.S. PATENT DOCUMENTS

| | | | | | |
|---|---|---|---|---|---|
| 5,393,670 | A | * | 2/1995 | Knowles et al. | 435/252.33 |
| 5,475,101 | A | * | 12/1995 | Ward et al. | 536/23.74 |
| 5,536,655 | A | * | 7/1996 | Thomas et al. | 435/209 |
| 5,723,328 | A | * | 3/1998 | Dalboege et al. | 435/209 |
| 5,919,691 | A | * | 7/1999 | Schulein et al. | 435/209 |
| 6,043,075 | A | * | 3/2000 | Bjornvad et al. | 435/209 |
| 6,074,867 | A | * | 6/2000 | Lam et al. | 435/277 |
| 6,110,720 | A | * | 8/2000 | Li et al. | 435/209 |
| 6,159,720 | A | * | 12/2000 | Murashima et al. | 435/209 |
| 6,207,436 | B1 | * | 3/2001 | Bjørnvad et al. | 435/209 |
| 7,045,331 | B2 | * | 5/2006 | Dunn-Coleman et al. | 435/209 |
| 7,056,721 | B2 | * | 6/2006 | Dunn-Coleman et al. | 435/209 |
| 7,138,263 | B2 | * | 11/2006 | Murashima et al. | 435/209 |
| 7,256,030 | B1 | * | 8/2007 | Schulein et al. | 435/209 |
| 7,361,495 | B2 | * | 4/2008 | Brown et al. | 435/209 |
| 7,465,571 | B1 | * | 12/2008 | Lam et al. | 435/209 |
| 7,741,074 | B2 | * | 6/2010 | Lopez de Leon et al. | 435/69.1 |
| 7,863,032 | B2 | * | 1/2011 | Berka et al. | 435/209 |
| 8,257,955 | B2 | * | 9/2012 | Moriya et al. | 435/209 |
| 2003/0113735 | A1 | * | 6/2003 | Dunn-Coleman et al. | 435/6 |
| 2003/0119167 | A1 | * | 6/2003 | Rasmussen et al. | 435/209 |
| 2005/0181485 | A1 | * | 8/2005 | Tsukamoto et al. | 435/101 |
| 2007/0256197 | A1 | * | 11/2007 | Brumm | 800/284 |
| 2008/0280325 | A1 | * | 11/2008 | Johansen et al. | 435/69.1 |
| 2008/0289067 | A1 | * | 11/2008 | Harris et al. | 800/298 |
| 2009/0328259 | A1 | * | 12/2009 | Harris et al. | 800/298 |
| 2010/0267089 | A1 | * | 10/2010 | Yang et al. | 435/72 |
| 2011/0047652 | A1 | * | 2/2011 | Lassen et al. | 800/298 |
| 2011/0061135 | A1 | * | 3/2011 | Krogh et al. | 800/298 |
| 2011/0185454 | A1 | * | 7/2011 | Harris et al. | 800/298 |
| 2011/0269212 | A1 | * | 11/2011 | Valtakari et al. | 435/209 |
| 2011/0269213 | A1 | * | 11/2011 | Puranen et al. | 435/209 |
| 2012/0151633 | A1 | * | 6/2012 | Lassen et al. | 800/298 |
| 2013/0023014 | A1 | * | 1/2013 | Yokoyama | 435/99 |
| 2013/0196387 | A1 | * | 8/2013 | Liu et al. | 435/99 |
| 2013/0212745 | A1 | * | 8/2013 | Spodsberg | 800/298 |
| 2013/0244292 | A1 | * | 9/2013 | Poland et al. | 435/99 |

FOREIGN PATENT DOCUMENTS

| | | | |
|---|---|---|---|
| WO | WO 9110732 A1 | * | 7/1991 |
| WO | WO 9428117 A1 | * | 12/1994 |
| WO | WO 03070940 A1 | * | 8/2003 |
| WO | WO 2009108941 A2 | * | 9/2009 |
| WO | WO 2011153516 A2 | * | 12/2011 |
| WO | WO 2012092676 A1 | * | 7/2012 |

OTHER PUBLICATIONS

Wymelenberg et al., "The *Phanerochaete chrysosporium* secretome: Database predictions and initial mass spectrometry peptide identifications in cellulose-grown medium", Journal of Biotechnology, vol. 118, pp. 17-34, 2005.*

Suzuki et al., "Comparative genomics of the white-rot fungi, *Phanerochaete carnosa* and *P. chrysosporum*, to elucidate the genetic basis of the distinct wood types they colonize", BMC Genomics, vol. 13, 444, 2012.*

Fernandez-Fueyo et al., "Comparative genomics of *Ceriporiopsis subvermispora* and *Phanerochaete chrysosporium* provide insight into selective ligninolysis", Proceedings of the National Academy of Sciences USA, vol. 109, No. 4, pp. 5458-5463, 2012.*

Eastwood et al., "The plant cell wall-decomposing machinery underlies the functional diversity of forest fungi", Science, vol. 333, pp. 762-765, 2011.*

Ohnishi et al., "Transcriptional regulation of two endoglucanase-encoding genes (cel3A and cel4) from the wood-degrading basidiomycete *Polyporus arcularius*", FEMS Microbiology Letters, vol. 274, pp. 218-225, 2007.*

Nozaki et al, "Structure and characteristics of an endo-beta-1,4-glucanase, isolated from *Trametes hirsuta*, with high degradation to crystalline cellulose", Biosciences, Biotechnology and Biochemistry, vol. 71, No. 10, pp. 2375-2382, 2007.*

Salinas et al., "Cloning of novel cellulase from cellulolytic fungi: Heterologous expression of a family 5 glycoside hydrolase from *Trametes versicolor* in *Pichia pastoris*", Enzyme and Microbial Technology, vol. 49, pp. 485-491, 2011.*

* cited by examiner

*Primary Examiner* — Rebecca Prouty
*Assistant Examiner* — Richard Ekstrom
(74) *Attorney, Agent, or Firm* — Elias Lambiris

(57) ABSTRACT

The present invention relates to isolated polypeptides having endoglucanase activity and polynucleotides encoding the polypeptides. The invention also relates to nucleic acid constructs, vectors, and host cells comprising the polynucleotides as well as methods of producing and using the polypeptides.

18 Claims, No Drawings

SEQUENCE LISTING

```
<160> NUMBER OF SEQ ID NOS: 8

<210> SEQ ID NO 1
<211> LENGTH: 1781
<212> TYPE: DNA
<213> ORGANISM: Trametes versicolor
<220> FEATURE:
<221> NAME/KEY: CDS
<222> LOCATION: (1)..(79)
<220> FEATURE:
<221> NAME/KEY: sig_peptide
<222> LOCATION: (1)..(63)
<220> FEATURE:
<221> NAME/KEY: mat_peptide
<222> LOCATION: (64)..()
```

-continued

```
<220> FEATURE:
<221> NAME/KEY: Intron
<222> LOCATION: (80)..(141)
<220> FEATURE:
<221> NAME/KEY: CDS
<222> LOCATION: (142)..(152)
<220> FEATURE:
<221> NAME/KEY: Intron
<222> LOCATION: (153)..(216)
<220> FEATURE:
<221> NAME/KEY: CDS
<222> LOCATION: (217)..(274)
<220> FEATURE:
<221> NAME/KEY: Intron
<222> LOCATION: (275)..(333)
<220> FEATURE:
<221> NAME/KEY: CDS
<222> LOCATION: (334)..(564)
<220> FEATURE:
<221> NAME/KEY: Intron
<222> LOCATION: (565)..(620)
<220> FEATURE:
<221> NAME/KEY: CDS
<222> LOCATION: (621)..(838)
<220> FEATURE:
<221> NAME/KEY: Intron
<222> LOCATION: (839)..(895)
<220> FEATURE:
<221> NAME/KEY: CDS
<222> LOCATION: (896)..(993)
<220> FEATURE:
<221> NAME/KEY: Intron
<222> LOCATION: (994)..(1049)
<220> FEATURE:
<221> NAME/KEY: CDS
<222> LOCATION: (1050)..(1133)
<220> FEATURE:
<221> NAME/KEY: Intron
<222> LOCATION: (1134)..(1183)
<220> FEATURE:
<221> NAME/KEY: CDS
<222> LOCATION: (1184)..(1345)
<220> FEATURE:
<221> NAME/KEY: Intron
<222> LOCATION: (1346)..(1409)
<220> FEATURE:
<221> NAME/KEY: CDS
<222> LOCATION: (1410)..(1585)
<220> FEATURE:
<221> NAME/KEY: Intron
<222> LOCATION: (1586)..(1638)
<220> FEATURE:
<221> NAME/KEY: CDS
<222> LOCATION: (1639)..(1778)

<400> SEQUENCE: 1 atg aag act ttc gca gcc ttg ctt tcc gct gtc act ctc gcg ctc tcg      48
Met Lys Thr Phe Ala Ala Leu Leu Ser Ala Val Thr Leu Ala Leu Ser
-20              -15                 -10 gtg cgc gcc cag gcg gct gtc tgg agt caa t gtaagtgccg ctgcttttca      99
Val Arg Ala Gln Ala Ala Val Trp Ser Gln
-5              -1 1             5 ttgatacgag actctacgcc gagctgacgt gctaccgtat ag gt  ggc ggt aca        152
                                                  Cys Gly Gly Thr gtaagttatc atagcatacc gcctacatgc acaaggacat actgctgatc aattctctgt    212 gcag ggt tgg acg ggc gag acc act tgc gtt gct ggt tcg gtt tgt acc    261
     Gly Trp Thr Gly Glu Thr Thr Cys Val Ala Gly Ser Val Cys Thr
         10                  15                  20 tcc ttg agc tca t gtgagcgact ttcaatccgt cgtcattgct cctcatgtat       314
Ser Leu Ser Ser
25 tgacgattgg ccttcatag ca  tac tct caa tgc gtt ccg ggc tcc gca acg    365
                         Tyr Ser Gln Cys Val Pro Gly Ser Ala Thr
```

```
                    Ser Tyr Ser Gln Cys Val Pro Gly Ser Ala Thr
                        30                  35 tcc agc gct ccg gcg gcc ccc tca gcg aca act tca ggc ccc gca cct       413
Ser Ser Ala Pro Ala Ala Pro Ser Ala Thr Thr Ser Gly Pro Ala Pro
40              45                  50                  55 cca gca tcc acg tgt gca ccc aac agc ccg ccc gcg agc gca ggc aaa       461
Pro Ala Ser Thr Cys Ala Pro Asn Ser Pro Pro Ala Ser Ala Gly Lys
                60                  65                  70 ctg cgc ttc gcg ggt gtc aac atc tcc ggt ttc gac ttc gga tgc agc       509
Leu Arg Phe Ala Gly Val Asn Ile Ser Gly Phe Asp Phe Gly Cys Ser
            75                  80                  85 acg gac gga acg tgc tcg gcc agc ggg gca tgg ccg cca ttg acc aag       557
Thr Asp Gly Thr Cys Ser Ala Ser Gly Ala Trp Pro Pro Leu Thr Lys
        90                  95                  100 tac tac g gtcagcccct tcctgcagg gtagtggcga gggtgttgac attttttgga      614
Tyr Tyr
    105 cgacag gc  atg gat ggt gcg ggc cag atg aag cac ttt gtc gag aac        661
        Gly Met Asp Gly Ala Gly Gln Met Lys His Phe Val Glu Asn
                            110                 115 gac ggc tac aat gtt ttc cgc ctg ccc gtt ggg tgg cag ttc ctg acg       709
Asp Gly Tyr Asn Val Phe Arg Leu Pro Val Gly Trp Gln Phe Leu Thr
120                 125                 130                 135 aac ggt gcc gcc act ggt gac ata gac gag gtc aac ttc gcc gag tac       757
Asn Gly Ala Ala Thr Gly Asp Ile Asp Glu Val Asn Phe Ala Glu Tyr
            140                 145                 150 gat gat ctc gtc caa gcg tgc ctc gac gca ggc gcg tcg tgc atc gtt       805
Asp Asp Leu Val Gln Ala Cys Leu Asp Ala Gly Ala Ser Cys Ile Val
        155                 160                 165 gag gtt cac aac tac gcg cgg ttt aac ggc aag gtacgatgcg cacttctgcg    858
Glu Val His Asn Tyr Ala Arg Phe Asn Gly Lys
    170                 175 agccagctga ctgtagccaa ccaaacctgg catacag atc atc ggt cag ggt ggg     913
                                        Ile Ile Gly Gln Gly Gly
                                                            180 ccc gca aat gac cag ttc gcc gcc ctt tgg agc agt ttt gcc tcc aag       961
Pro Ala Asn Asp Gln Phe Ala Ala Leu Trp Ser Ser Phe Ala Ser Lys
185                 190                 195                 200 tac gcc gac aac gac aag atc atc ttt ggg at  gtcagtgcct tttccggatt    1013
Tyr Ala Asp Asn Asp Lys Ile Ile Phe Gly Ile
            205                 210 ccgcaaactg tagctcatgc aataaccgac tcacag t atg aac gaa cca cat gac    1068
                                          Met Asn Glu Pro His Asp
                                                          215 gtc ccc gat atc aac ctc tgg gcg gag agt gtc cag gca gca gtg acc       1116
Val Pro Asp Ile Asn Leu Trp Ala Glu Ser Val Gln Ala Ala Val Thr
            220                 225                 230 gcc atc cgc cag gcc gg  gtatgcatgt caaccccaaa accaaatgct              1163
Ala Ile Arg Gln Ala Gly
        235 gctcactaat cggtccctag t gcg act tcg cag ctg atc ctg ctc ccg ggc      1214
                       Ala Thr Ser Gln Leu Ile Leu Leu Pro Gly
                           240                 245 aac aac tgg acg tct gcg gag acc ttc gtc tcc aac ggc tcg gcc gat       1262
Asn Asn Trp Thr Ser Ala Glu Thr Phe Val Ser Asn Gly Ser Ala Asp
250                 255                 260                 265 gcg ctc aac aag gtc acg aac ccc gac ggc agc atc acg aac ctc atc       1310
Ala Leu Asn Lys Val Thr Asn Pro Asp Gly Ser Ile Thr Asn Leu Ile
            270                 275                 280
```

```
ttc gac gtg cac aag tac ctc gac ttc gac aac tc gtacgtctat      1355
Phe Asp Val His Lys Tyr Leu Asp Phe Asp Asn Ser
            285                 290 gcccacttgc cccgttgatt ctgcaggtga attgacgtaa tgcggatcgc acag g ggc   1413
                                                             Gly acg aac gca gag tgc acg acg aac aac atc gac aac gcg tgg gcg ccg     1461
Thr Asn Ala Glu Cys Thr Thr Asn Asn Ile Asp Asn Ala Trp Ala Pro
295                 300                 305                 310 ctc gcg cag tgg ctg cgc tgc aac ggc cgg cag gcg ttc aac acc gag    1509
Leu Ala Gln Trp Leu Arg Cys Asn Gly Arg Gln Ala Phe Asn Thr Glu
                315                 320                 325 acg ggc ggc ggg aac gtc gcg tcg tgc gag acg ttc atg tgc gag cag    1557
Thr Gly Gly Gly Asn Val Ala Ser Cys Glu Thr Phe Met Cys Glu Gln
                330                 335                 340 gtc gcg ttc cag acg gcg aac tcg gac g gtgcgttctg cgtcctcgcg        1605
Val Ala Phe Gln Thr Ala Asn Ser Asp
                345                 350 tcgttcttca ctctcgctga tgatatcgtg tag tg  ttc ttg ggc tat gtc ggc   1658
                                        Val Phe Leu Gly Tyr Val Gly
                                                            355 tgg gcg gcg ggc aac ttc tac gaa ggc tac gtg ctg agc gag gtc ccg    1706
Trp Ala Ala Gly Asn Phe Tyr Glu Gly Tyr Val Leu Ser Glu Val Pro
        360                 365                 370 acc cag aat gcg gat ggg agc tgg acg gac cag ccg ctt gtt gcg cag    1754
Thr Gln Asn Ala Asp Gly Ser Trp Thr Asp Gln Pro Leu Val Ala Gln
375                 380                 385                 390 tgc atg gcg ccc aac gct tct cag tga                                1781
Cys Met Ala Pro Asn Ala Ser Gln
                395

<210> SEQ ID NO 2
<211> LENGTH: 419
<212> TYPE: PRT
<213> ORGANISM: Trametes versicolor

<400> SEQUENCE: 2

Met Lys Thr Phe Ala Ala Leu Leu Ser Ala Val Thr Leu Ala Leu Ser
    -20              -15                 -10

Val Arg Ala Gln Ala Ala Val Trp Ser Gln Cys Gly Gly Thr Gly Trp
-5               -1  1               5                   10

Thr Gly Glu Thr Thr Cys Val Ala Gly Ser Val Cys Ser Leu Ser
            15                  20                  25

Ser Ser Tyr Ser Gln Cys Val Pro Gly Ser Ala Thr Ser Ser Ala Pro
            30                  35                  40

Ala Ala Pro Ser Ala Thr Thr Ser Gly Pro Ala Pro Pro Ala Ser Thr
        45                  50                  55

Cys Ala Pro Asn Ser Pro Pro Ala Ser Ala Gly Lys Leu Arg Phe Ala
60                  65                  70                  75

Gly Val Asn Ile Ser Gly Phe Asp Phe Gly Cys Ser Thr Asp Gly Thr
                80                  85                  90

Cys Ser Ala Ser Gly Ala Trp Pro Pro Leu Thr Lys Tyr Tyr Gly Met
            95                  100                 105

Asp Gly Ala Gly Gln Met Lys His Phe Val Glu Asn Asp Gly Tyr Asn
        110                 115                 120

Val Phe Arg Leu Pro Val Gly Trp Gln Phe Leu Thr Asn Gly Ala Ala
        125                 130                 135

Thr Gly Asp Ile Asp Glu Val Asn Phe Ala Glu Tyr Asp Asp Leu Val
140                 145                 150                 155
```

```
Gln Ala Cys Leu Asp Ala Gly Ala Ser Cys Ile Val Glu Val His Asn
                160                 165                 170
Tyr Ala Arg Phe Asn Gly Lys Ile Ile Gly Gln Gly Gly Pro Ala Asn
            175                 180                 185
Asp Gln Phe Ala Ala Leu Trp Ser Ser Phe Ala Ser Lys Tyr Ala Asp
        190                 195                 200
Asn Asp Lys Ile Ile Phe Gly Ile Met Asn Glu Pro His Asp Val Pro
    205                 210                 215
Asp Ile Asn Leu Trp Ala Glu Ser Val Gln Ala Ala Val Thr Ala Ile
220                 225                 230                 235
Arg Gln Ala Gly Ala Thr Ser Gln Leu Ile Leu Leu Pro Gly Asn Asn
                240                 245                 250
Trp Thr Ser Ala Glu Thr Phe Val Ser Asn Gly Ser Ala Asp Ala Leu
            255                 260                 265
Asn Lys Val Thr Asn Pro Asp Gly Ser Ile Thr Asn Leu Ile Phe Asp
        270                 275                 280
Val His Lys Tyr Leu Asp Phe Asp Asn Ser Gly Thr Asn Ala Glu Cys
    285                 290                 295
Thr Thr Asn Asn Ile Asp Asn Ala Trp Ala Pro Leu Ala Gln Trp Leu
300                 305                 310                 315
Arg Cys Asn Gly Arg Gln Ala Phe Asn Thr Glu Thr Gly Gly Gly Asn
                320                 325                 330
Val Ala Ser Cys Glu Thr Phe Met Cys Glu Gln Val Ala Phe Gln Thr
            335                 340                 345
Ala Asn Ser Asp Val Phe Leu Gly Tyr Val Gly Trp Ala Ala Gly Asn
        350                 355                 360
Phe Tyr Glu Gly Tyr Val Leu Ser Glu Val Pro Thr Gln Asn Ala Asp
    365                 370                 375
Gly Ser Trp Thr Asp Gln Pro Leu Val Ala Gln Cys Met Ala Pro Asn
380                 385                 390                 395
Ala Ser Gln

<210> SEQ ID NO 3
<211> LENGTH: 1785
<212> TYPE: DNA
<213> ORGANISM: Trametes versicolor
<220> FEATURE:
<221> NAME/KEY: CDS
<222> LOCATION: (1)..(84)
<220> FEATURE:
<221> NAME/KEY: sig_peptide
<222> LOCATION: (1)..(60)
<220> FEATURE:
<221> NAME/KEY: mat_peptide
<222> LOCATION: (61)..()
<220> FEATURE:
<221> NAME/KEY: Intron
<222> LOCATION: (85)..(144)
<220> FEATURE:
<221> NAME/KEY: CDS
<222> LOCATION: (145)..(208)
<220> FEATURE:
<221> NAME/KEY: Intron
<222> LOCATION: (209)..(265)
<220> FEATURE:
<221> NAME/KEY: CDS
<222> LOCATION: (266)..(459)
<220> FEATURE:
<221> NAME/KEY: Intron
<222> LOCATION: (460)..(531)
<220> FEATURE:
<221> NAME/KEY: CDS
```

-continued

```
<222> LOCATION: (532)..(700)
<220> FEATURE:
<221> NAME/KEY: Intron
<222> LOCATION: (701)..(759)
<220> FEATURE:
<221> NAME/KEY: CDS
<222> LOCATION: (760)..(808)
<220> FEATURE:
<221> NAME/KEY: Intron
<222> LOCATION: (809)..(861)
<220> FEATURE:
<221> NAME/KEY: CDS
<222> LOCATION: (862)..(872)
<220> FEATURE:
<221> NAME/KEY: Intron
<222> LOCATION: (873)..(930)
<220> FEATURE:
<221> NAME/KEY: CDS
<222> LOCATION: (931)..(956)
<220> FEATURE:
<221> NAME/KEY: Intron
<222> LOCATION: (957)..(1018)
<220> FEATURE:
<221> NAME/KEY: CDS
<222> LOCATION: (1019)..(1093)
<220> FEATURE:
<221> NAME/KEY: Intron
<222> LOCATION: (1094)..(1155)
<220> FEATURE:
<221> NAME/KEY: CDS
<222> LOCATION: (1156)..(1312)
<220> FEATURE:
<221> NAME/KEY: Intron
<222> LOCATION: (1313)..(1383)
<220> FEATURE:
<221> NAME/KEY: CDS
<222> LOCATION: (1384)..(1640)
<220> FEATURE:
<221> NAME/KEY: Intron
<222> LOCATION: (1641)..(1710)
<220> FEATURE:
<221> NAME/KEY: CDS
<222> LOCATION: (1711)..(1782)

<400> SEQUENCE: 3 atg aag acg gtt atc ctc tcc ctc gct gcc gcg ctc ttc agc gcc gcg      48
Met Lys Thr Val Ile Leu Ser Leu Ala Ala Ala Leu Phe Ser Ala Ala
-20              -15                 -10                 -5 ccc gtg ctc tcc acc gcc gtc tgg ggc cag tgc ggc gtgagtactc           94
Pro Val Leu Ser Thr Ala Val Trp Gly Gln Cys Gly
       -1   1               5 gactcgcgac gcggtcacgg ggccatactc accatctgct cgtgttctag ggc act      150
                                                        Gly Thr
                                                            10 ggc ttc tct ggc gac acg acc tgc gcc tcc ggc tct agc tgc gtc gta    198
Gly Phe Ser Gly Asp Thr Thr Cys Ala Ser Gly Ser Ser Cys Val Val
            15                  20                  25 gtc aac caa t gtatgccgtc cacgtccacc cgctgacatc ctttactgac           248
Val Asn Gln cactcaccct tgaacag ac  tac tcg caa tgc cag ccc ggc gcg tcc gcc     297
                    Tyr Tyr Ser Gln Cys Gln Pro Gly Ala Ser Ala
                        30                  35                  40 ccc acg tcg act gcc tcg gcc ccc ggc cct tcc ggc tgc tcg ggc acg    345
Pro Thr Ser Thr Ala Ser Ala Pro Gly Pro Ser Gly Cys Ser Gly Thr
                45                  50                  55 cgc acc aag ttc aag ctc ttc ggt gtg aac gag tcc ggc gcg gag ttc    393
Arg Thr Lys Phe Lys Leu Phe Gly Val Asn Glu Ser Gly Ala Glu Phe
        60                  65                  70 ggg aac acc gtc atc ccg ggc gcg ctc ggc acg gac tac acc tgg ccg    441
Gly Asn Thr Val Ile Pro Gly Ala Leu Gly Thr Asp Tyr Thr Trp Pro
```

```
                    75                  80                  85
tcg ccc acc tcc atc gac gtgcgtactg ttgtcggaca tgtctgacgt            489
Ser Pro Thr Ser Ile Asp
     90 agaagcagag gatgctgatg gatggacggt tgggcgatgc ag ttc ttc ctc ggg     543
                                                Phe Phe Leu Gly
                                                         95 cag ggc ttc aac acc ttc cgc atc ccg ttc ctg atg gag cgc gtc agc    591
Gln Gly Phe Asn Thr Phe Arg Ile Pro Phe Leu Met Glu Arg Val Ser
        100                 105                 110 ccg ccg tcg acg ggc ggc ctt act ggc ccg ttc aac agc acg tac ctc    639
Pro Pro Ser Thr Gly Gly Leu Thr Gly Pro Phe Asn Ser Thr Tyr Leu
115                 120                 125                 130 gac ggg ctg aag cag act gtt agc tac atc acg ggc aag ggg ggc ttt    687
Asp Gly Leu Lys Gln Thr Val Ser Tyr Ile Thr Gly Lys Gly Gly Phe
                135                 140                 145 gcc atc gtc gac c gtgagtgctt actcccaacg tatgctattt ggagagtgga      740
Ala Ile Val Asp
            150 gtactgatct ggtgtgcag cg cac aac ttc atg atc ttc aac ggc gcg acg    791
                       Pro His Asn Phe Met Ile Phe Asn Gly Ala Thr
                                            155                 160 atc acg agc acc agc ca gtaagtcgca ttatttacgg tggaagagtt            838
Ile Thr Ser Thr Ser Gln
                165 ttactgatat ctatcgcgtt tag g ttc cag gct t gtacgtattc gcgtcgccat    892
                            Phe Gln Ala
                                    170 atacacgaca ccgagctctt tgctgatgtt gacgacag gg tgg cag aag ctc gct   947
                                             Trp Trp Gln Lys Leu Ala
                                                                175 gct gag ttc gtgagtgtgc tccatggcta cgcggccgtg aacgctctgg            996
Ala Glu Phe ctgacaagat gccgcctccc ag aaa acc gac aac aac gtc atc ttc gac ctg   1048
                          Lys Thr Asp Asn Asn Val Ile Phe Asp Leu
                                180                 185 atg aac gag ccg cac gac atc ccc gcg cag acc gtc ttc cag ctc        1093
Met Asn Glu Pro His Asp Ile Pro Ala Gln Thr Val Phe Gln Leu
190                 195                 200 gtacgtaaca ctttccgtat gtcccaagca accatgtgtt aagtgatcat gatcccgcgc  1153 ag atg caa gcg gcc gtg aac ggc gtg cgc gcg agc ggc gcg acg agc     1200
   Met Gln Ala Ala Val Asn Gly Val Arg Ala Ser Gly Ala Thr Ser
       205                 210                 215 cag ctc atc ctc gcc gag ggc acg agc tgg acc ggc gcg tgg acc tgg    1248
Gln Leu Ile Leu Ala Glu Gly Thr Ser Trp Thr Gly Ala Trp Thr Trp
220                 225                 230                 235 acg acg tcg ggc aac agc gac gcg ttc ggc gcg atc aag gac ccc aac    1296
Thr Thr Ser Gly Asn Ser Asp Ala Phe Gly Ala Ile Lys Asp Pro Asn
                240                 245                 250 aac aac atc gcc atc c gtgcgtcccc ccctcccc ttcctcttgc ccctgccta     1352
Asn Asn Ile Ala Ile
                255 ctgacgaaca cgccatggga ttgacacaca g ag atg cac cag tac cta gac      1403
                                    Gln Met His Gln Tyr Leu Asp
                                                     260 tcg gac ggg tcg ggg acg tcc ccg atc tgc gtg tcg gac acg atc ggg    1451
Ser Asp Gly Ser Gly Thr Ser Pro Ile Cys Val Ser Asp Thr Ile Gly
265                 270                 275
```

```
gcg gag cgg ctg cag gcg gcg acg cag tgg ctg cag cag acg ggc ctc      1499
Ala Glu Arg Leu Gln Ala Ala Thr Gln Trp Leu Gln Gln Thr Gly Leu
280                 285                 290                 295 aag ggc ttc ctc ggc gag atc ggg acg ggg aac aac acg cag tgc gtg      1547
Lys Gly Phe Leu Gly Glu Ile Gly Thr Gly Asn Asn Thr Gln Cys Val
                300                 305                 310 acc gcg ctg cag ggc gcg ctg tgc gag atg cag cag gcg ggc ggg acg      1595
Thr Ala Leu Gln Gly Ala Leu Cys Glu Met Gln Gln Ala Gly Gly Thr
            315                 320                 325 tgg ctc ggc gcg ctc tgg tgg gcg gcg ggg ccg tgg tgg gga gac          1640
Trp Leu Gly Ala Leu Trp Trp Ala Ala Gly Pro Trp Trp Gly Asp
        330                 335                 340 gtgagtggct ttctgtgctt atgtggggga ggggagtgg gggctgacgg tggttgtgtt     1700
ggacttgcag tac tac cag agc atc gag ccc ccg aac ggg gac gcg atc       1749
            Tyr Tyr Gln Ser Ile Glu Pro Pro Asn Gly Asp Ala Ile
                345                 350                 355 gct gcg atc ctc ccg gcg ctc aag gcg ttc cag tag                      1785
Ala Ala Ile Leu Pro Ala Leu Lys Ala Phe Gln
            360                 365

<210> SEQ ID NO 4
<211> LENGTH: 386
<212> TYPE: PRT
<213> ORGANISM: Trametes versicolor

<400> SEQUENCE: 4

Met Lys Thr Val Ile Leu Ser Leu Ala Ala Ala Leu Phe Ser Ala Ala
-20                 -15                 -10                 -5

Pro Val Leu Ser Thr Ala Val Trp Gly Gln Cys Gly Gly Thr Gly Phe
            -1  1                   5                   10

Ser Gly Asp Thr Thr Cys Ala Ser Gly Ser Ser Cys Val Val Val Asn
                15                  20                  25

Gln Tyr Tyr Ser Gln Cys Gln Pro Gly Ala Ser Ala Pro Thr Ser Thr
            30                  35                  40

Ala Ser Ala Pro Gly Pro Ser Gly Cys Ser Gly Thr Arg Thr Lys Phe
45                  50                  55                  60

Lys Leu Phe Gly Val Asn Glu Ser Gly Ala Glu Phe Gly Asn Thr Val
                65                  70                  75

Ile Pro Gly Ala Leu Gly Thr Asp Tyr Thr Trp Pro Ser Pro Thr Ser
            80                  85                  90

Ile Asp Phe Phe Leu Gly Gln Gly Phe Asn Thr Phe Arg Ile Pro Phe
        95                  100                 105

Leu Met Glu Arg Val Ser Pro Pro Ser Thr Gly Gly Leu Thr Gly Pro
    110                 115                 120

Phe Asn Ser Thr Tyr Leu Asp Gly Leu Lys Gln Thr Val Ser Tyr Ile
125                 130                 135                 140

Thr Gly Lys Gly Gly Phe Ala Ile Val Asp Pro His Asn Phe Met Ile
                145                 150                 155

Phe Asn Gly Ala Thr Ile Thr Ser Ser Gln Phe Gln Ala Trp Trp
            160                 165                 170

Gln Lys Leu Ala Ala Glu Phe Lys Thr Asp Asn Asn Val Ile Phe Asp
        175                 180                 185

Leu Met Asn Glu Pro His Asp Ile Pro Ala Gln Thr Val Phe Gln Leu
    190                 195                 200

Met Gln Ala Ala Val Asn Gly Val Arg Ala Ser Gly Ala Thr Ser Gln
205                 210                 215                 220
```

```
Leu Ile Leu Ala Glu Gly Thr Ser Trp Thr Gly Ala Trp Thr Trp Thr
                225                 230                 235
Thr Ser Gly Asn Ser Asp Ala Phe Gly Ala Ile Lys Asp Pro Asn Asn
            240                 245                 250
Asn Ile Ala Ile Gln Met His Gln Tyr Leu Asp Ser Asp Gly Ser Gly
        255                 260                 265
Thr Ser Pro Ile Cys Val Ser Asp Thr Ile Gly Ala Glu Arg Leu Gln
    270                 275                 280
Ala Ala Thr Gln Trp Leu Gln Gly Thr Gly Leu Lys Gly Phe Leu Gly
285                 290                 295                 300
Glu Ile Gly Thr Gly Asn Asn Thr Gln Cys Val Thr Ala Leu Gln Gly
                305                 310                 315
Ala Leu Cys Glu Met Gln Gln Ala Gly Gly Thr Trp Leu Gly Ala Leu
            320                 325                 330
Trp Trp Ala Ala Gly Pro Trp Trp Gly Asp Tyr Tyr Gln Ser Ile Glu
        335                 340                 345
Pro Pro Asn Gly Asp Ala Ile Ala Ile Leu Pro Ala Leu Lys Ala
    350                 355                 360
Phe Gln
365

<210> SEQ ID NO 5
<211> LENGTH: 1772
<212> TYPE: DNA
<213> ORGANISM: Trametes versicolor
<220> FEATURE:
<221> NAME/KEY: CDS
<222> LOCATION: (1)..(57)
<220> FEATURE:
<221> NAME/KEY: sig_peptide
<222> LOCATION: (1)..(57)
<220> FEATURE:
<221> NAME/KEY: Intron
<222> LOCATION: (58)..(111)
<220> FEATURE:
<221> NAME/KEY: mat_peptide
<222> LOCATION: (112)..()
<220> FEATURE:
<221> NAME/KEY: CDS
<222> LOCATION: (112)..(142)
<220> FEATURE:
<221> NAME/KEY: Intron
<222> LOCATION: (143)..(195)
<220> FEATURE:
<221> NAME/KEY: CDS
<222> LOCATION: (196)..(246)
<220> FEATURE:
<221> NAME/KEY: Intron
<222> LOCATION: (247)..(301)
<220> FEATURE:
<221> NAME/KEY: CDS
<222> LOCATION: (302)..(408)
<220> FEATURE:
<221> NAME/KEY: Intron
<222> LOCATION: (409)..(462)
<220> FEATURE:
<221> NAME/KEY: CDS
<222> LOCATION: (463)..(556)
<220> FEATURE:
<221> NAME/KEY: Intron
<222> LOCATION: (557)..(612)
<220> FEATURE:
<221> NAME/KEY: CDS
<222> LOCATION: (613)..(618)
<220> FEATURE:
<221> NAME/KEY: Intron
<222> LOCATION: (619)..(668)
<220> FEATURE:
<221> NAME/KEY: CDS
```

```
<222> LOCATION: (669)..(909)
<220> FEATURE:
<221> NAME/KEY: Intron
<222> LOCATION: (910)..(974)
<220> FEATURE:
<221> NAME/KEY: CDS
<222> LOCATION: (975)..(1192)
<220> FEATURE:
<221> NAME/KEY: Intron
<222> LOCATION: (1193)..(1244)
<220> FEATURE:
<221> NAME/KEY: CDS
<222> LOCATION: (1245)..(1297)
<220> FEATURE:
<221> NAME/KEY: Intron
<222> LOCATION: (1298)..(1361)
<220> FEATURE:
<221> NAME/KEY: CDS
<222> LOCATION: (1362)..(1471)
<220> FEATURE:
<221> NAME/KEY: Intron
<222> LOCATION: (1472)..(1539)
<220> FEATURE:
<221> NAME/KEY: CDS
<222> LOCATION: (1540)..(1688)
<220> FEATURE:
<221> NAME/KEY: Intron
<222> LOCATION: (1689)..(1752)
<220> FEATURE:
<221> NAME/KEY: CDS
<222> LOCATION: (1753)..(1769)

<400> SEQUENCE: 5 atg aag tac gca act gcc tct ctc gtg gct gcg gcc acc gtc tcc cag        48
Met Lys Tyr Ala Thr Ala Ser Leu Val Ala Ala Ala Thr Val Ser Gln
            -15                 -10                 -5 gtt atg gcg gtatgcactc aggctagtac ttcacatgct ggattatact                 97
Val Met Ala
        -1 cattagcaac gtag gtg tac caa cag tgc ggt ggt atc ggt ttc g              142
                Val Tyr Gln Gln Cys Gly Gly Ile Gly Phe
                 1               5                  10 gttagcagaa ttgcaagtgg cgcatttgac tgcccttgct aacgaacttg cag at          197
                                                            Asp agg ccc act gct tgt gat gct cac tcg gtg tgc act gct atc aat ccc c      246
Arg Pro Thr Ala Cys Asp Ala His Ser Val Cys Thr Ala Ile Asn Pro
             15                  20                  25 gtatgtctgt cctgctatca ttacacagac atagtaggct catgctggca tgcag ac         303
                                                              His tac tcc cag tgc ctc ccg tcg tct tcc ccc tcg gcg ccc tct gcc ccc        351
Tyr Ser Gln Cys Leu Pro Ser Ser Ser Pro Ser Ala Pro Ser Ala Pro
         30                  35                  40 cgc tcc agc ctg atc cag ctc ggt ggt gtc aac act gcg gga tac gac        399
Arg Ser Ser Leu Ile Gln Leu Gly Gly Val Asn Thr Ala Gly Tyr Asp
 45                  50                  55                  60 ttc agc gtt gtacgtcctc tgaaacaaaa gtcttagacc cattgctcac                448
Phe Ser Val agatattgac atag act att gac gga agc ttc acc ggc acc ggt gtc tct        498
              Thr Ile Asp Gly Ser Phe Thr Gly Thr Gly Val Ser
                       65                  70                  75 ccc ccg ccc tct cag tat acc cac ttc tct agc cag ggt gcc aac ctc        546
Pro Pro Pro Ser Gln Tyr Thr His Phe Ser Ser Gln Gly Ala Asn Leu
                 80                  85                  90 ttc cgc att c gtgagtgtgc caagtgttga gtacgggaat aatactgatc              596
Phe Arg Ile atattttttg ccgtag cc  ttc g gtgcgttctc tgtctagcga tgtggtttcg           648
```

```
                        Pro Phe
                            95 ttctcatagc cctcctttag cc  tgg cag ctg atg acg ccg aac gtc ggc gga      700
                          Ala Trp Gln Leu Met Thr Pro Asn Val Gly Gly
                              100                 105 ccc atc aac gag acg ttc ttc gcc acc tat gac aag acc gtc cag gct        748
Pro Ile Asn Glu Thr Phe Phe Ala Thr Tyr Asp Lys Thr Val Gln Ala
        110                 115                 120 gcg ctc aac tcg ggc tcc aac gtg cac gtc atc atc gat ctg cac aac        796
Ala Leu Asn Ser Gly Ser Asn Val His Val Ile Ile Asp Leu His Asn
    125                 130                 135 tat gcg cgc tgg aac ggc gcc atc atc gct caa ggc ggc ccg acc aac        844
Tyr Ala Arg Trp Asn Gly Ala Ile Ile Ala Gln Gly Gly Pro Thr Asn
140                 145                 150                 155 gag caa ttt gct tcc atc tgg acc cag ctc gcc gcc aag tac ggc cgc        892
Glu Gln Phe Ala Ser Ile Trp Thr Gln Leu Ala Ala Lys Tyr Gly Arg
                160                 165                 170 aac aag cgt atc atc tt  gtacgctcct tcctccctct ctttcttatg               939
Asn Lys Arg Ile Ile Phe
                175 acatgtatga ggatagctgc tgacgacgtc cgcag c ggt ctc atg aac gag cca       993
                                        Gly Leu Met Asn Glu Pro
                                                        180 cac gac ctc ccc agc gtc ccg acc tgg gtt aag tct gtc cag ttc gtt       1041
His Asp Leu Pro Ser Val Pro Thr Trp Val Lys Ser Val Gln Phe Val
    185                 190                 195 gtc aac gcc atc cgc cat gcc ggc gcg acg aac ttc ctc ctc ctg cct       1089
Val Asn Ala Ile Arg His Ala Gly Ala Thr Asn Phe Leu Leu Leu Pro
200                 205                 210                 215 ggc tcc agc ttc tca tcc gcc cag gcc ttc ccc acc gag gcc ggc cct       1137
Gly Ser Ser Phe Ser Ser Ala Gln Ala Phe Pro Thr Glu Ala Gly Pro
                220                 225                 230 gac ctc gtc aag gtc act gac ccg ctc ggc ggc acc cac aag ctg atc       1185
Asp Leu Val Lys Val Thr Asp Pro Leu Gly Gly Thr His Lys Leu Ile
            235                 240                 245 ttc gat g gtaggtttag cgtgttagaa cccatcctgt gccggactga cctctgccgc      1242
Phe Asp ag tc  cac aag tat ctc gac agc gac aac agc ggc act cac ccc gac        1288
       Val His Lys Tyr Leu Asp Ser Asp Asn Ser Gly Thr His Pro Asp
                   250                 255                 260 tgc acc act gtacgttgca ccgccccgtc tatcacgaac gcgacttcca               1337
Cys Thr Thr
265 gcgatgctca tgcacattcc atag gac aac gtc gac gtg ctg aag acg ctc        1388
                          Asp Asn Val Asp Val Leu Lys Thr Leu
                                        270                 275 gtc cag ttc ctc aag cag aac ggc aac cgc cag gcg ctc ctc agc gag       1436
Val Gln Phe Leu Lys Gln Asn Gly Asn Arg Gln Ala Leu Leu Ser Glu
            280                 285                 290 acc ggc gga gga aac acc acg agc tgc gag act ct  gtaagtgcca            1481
Thr Gly Gly Gly Asn Thr Thr Ser Cys Glu Thr Leu
                295                 300 gtggccttgc acgccgccca cttgggcttg tagtagcacg ctgacgcact ccccgaag c     1540 ctc aac acc gag ctc tcg ttc gtc aag tcc gcg ttc ccg acc ctc gtc       1588
Leu Asn Thr Glu Leu Ser Phe Val Lys Ser Ala Phe Pro Thr Leu Val
305                 310                 315                 320 ggc ttc tcc gcc tgg gcc gcc ggc gcg ttc gac acc aac tac gtg ctc       1636
Gly Phe Ser Ala Trp Ala Ala Gly Ala Phe Asp Thr Asn Tyr Val Leu
                325                 330                 335
```

```
acg ctc acg ccc aac gcc gac ggc tcc gac cag ccc ctc tgg atc gac     1684
Thr Leu Thr Pro Asn Ala Asp Gly Ser Asp Gln Pro Leu Trp Ile Asp
        340                 345                 350 gcc g gtacgtgtgg ccctgccagt gctcattctg tcctctcgat ataggtgctc         1738
Ala accattcgct gcag tc aag ccc aac ctg cct tga                           1772
                Val Lys Pro Asn Leu Pro
                    355
```

<210> SEQ ID NO 6
<211> LENGTH: 378
<212> TYPE: PRT
<213> ORGANISM: Trametes versicolor

<400> SEQUENCE: 6

```
Met Lys Tyr Ala Thr Ala Ser Leu Val Ala Ala Thr Val Ser Gln
            -15                 -10                 -5

Val Met Ala Val Tyr Gln Gln Cys Gly Gly Ile Gly Phe Asp Arg Pro
        -1  1              5                  10

Thr Ala Cys Asp Ala His Ser Val Cys Thr Ala Ile Asn Pro His Tyr
         15                 20                  25

Ser Gln Cys Leu Pro Ser Ser Pro Ser Ala Pro Ser Ala Pro Arg
 30              35                  40                  45

Ser Ser Leu Ile Gln Leu Gly Gly Val Asn Thr Ala Gly Tyr Asp Phe
             50                  55                      60

Ser Val Thr Ile Asp Gly Ser Phe Thr Gly Thr Gly Val Ser Pro Pro
             65                  70                  75

Pro Ser Gln Tyr Thr His Phe Ser Ser Gln Gly Ala Asn Leu Phe Arg
         80                  85                  90

Ile Pro Phe Ala Trp Gln Leu Met Thr Pro Asn Val Gly Gly Pro Ile
 95                 100                 105

Asn Glu Thr Phe Phe Ala Thr Tyr Asp Lys Thr Val Gln Ala Ala Leu
110                 115                 120                 125

Asn Ser Gly Ser Asn Val His Val Ile Ile Asp Leu His Asn Tyr Ala
                130                 135                 140

Arg Trp Asn Gly Ala Ile Ile Ala Gln Gly Gly Pro Thr Asn Glu Gln
            145                 150                 155

Phe Ala Ser Ile Trp Thr Gln Leu Ala Ala Lys Tyr Gly Arg Asn Lys
        160                 165                 170

Arg Ile Ile Phe Gly Leu Met Asn Glu Pro His Asp Leu Pro Ser Val
175                 180                 185

Pro Thr Trp Val Lys Ser Val Gln Phe Val Val Asn Ala Ile Arg His
190                 195                 200                 205

Ala Gly Ala Thr Asn Phe Leu Leu Leu Pro Gly Ser Ser Phe Ser Ser
                210                 215                 220

Ala Gln Ala Phe Pro Thr Glu Ala Gly Pro Asp Leu Val Lys Val Thr
                225                 230                 235

Asp Pro Leu Gly Gly Thr His Lys Leu Ile Phe Asp Val His Lys Tyr
        240                 245                 250

Leu Asp Ser Asp Asn Ser Gly Thr His Pro Asp Cys Thr Thr Asp Asn
255                 260                 265

Val Asp Val Leu Lys Thr Leu Val Gln Phe Leu Lys Gln Asn Gly Asn
270                 275                 280                 285

Arg Gln Ala Leu Leu Ser Glu Thr Gly Gly Gly Asn Thr Thr Ser Cys
                290                 295                 300
```

Glu Thr Leu Leu Asn Thr Glu Leu Ser Phe Val Lys Ser Ala Phe Pro
            305                 310                 315

Thr Leu Val Gly Phe Ser Ala Trp Ala Ala Gly Ala Phe Asp Thr Asn
        320                 325                 330

Tyr Val Leu Thr Leu Thr Pro Asn Ala Asp Gly Ser Asp Gln Pro Leu
        335                 340                 345

Trp Ile Asp Ala Val Lys Pro Asn Leu Pro
350                 355

<210> SEQ ID NO 7
<211> LENGTH: 1746
<212> TYPE: DNA
<213> ORGANISM: Trametes versicolor
<220> FEATURE:
<221> NAME/KEY: CDS
<222> LOCATION: (1)..(57)
<220> FEATURE:
<221> NAME/KEY: sig_peptide
<222> LOCATION: (1)..(57)
<220> FEATURE:
<221> NAME/KEY: Intron
<222> LOCATION: (58)..(108)
<220> FEATURE:
<221> NAME/KEY: mat_peptide
<222> LOCATION: (109)..()
<220> FEATURE:
<221> NAME/KEY: CDS
<222> LOCATION: (109)..(139)
<220> FEATURE:
<221> NAME/KEY: Intron
<222> LOCATION: (140)..(192)
<220> FEATURE:
<221> NAME/KEY: CDS
<222> LOCATION: (193)..(243)
<220> FEATURE:
<221> NAME/KEY: Intron
<222> LOCATION: (244)..(295)
<220> FEATURE:
<221> NAME/KEY: CDS
<222> LOCATION: (296)..(402)
<220> FEATURE:
<221> NAME/KEY: Intron
<222> LOCATION: (403)..(456)
<220> FEATURE:
<221> NAME/KEY: CDS
<222> LOCATION: (457)..(550)
<220> FEATURE:
<221> NAME/KEY: Intron
<222> LOCATION: (551)..(606)
<220> FEATURE:
<221> NAME/KEY: CDS
<222> LOCATION: (607)..(612)
<220> FEATURE:
<221> NAME/KEY: Intron
<222> LOCATION: (613)..(665)
<220> FEATURE:
<221> NAME/KEY: CDS
<222> LOCATION: (666)..(906)
<220> FEATURE:
<221> NAME/KEY: Intron
<222> LOCATION: (907)..(968)
<220> FEATURE:
<221> NAME/KEY: CDS
<222> LOCATION: (969)..(1186)
<220> FEATURE:
<221> NAME/KEY: Intron
<222> LOCATION: (1187)..(1238)
<220> FEATURE:
<221> NAME/KEY: CDS
<222> LOCATION: (1239)..(1291)
<220> FEATURE:
<221> NAME/KEY: Intron

```
<222> LOCATION: (1292)..(1352)
<220> FEATURE:
<221> NAME/KEY: CDS
<222> LOCATION: (1353)..(1462)
<220> FEATURE:
<221> NAME/KEY: Intron
<222> LOCATION: (1463)..(1519)
<220> FEATURE:
<221> NAME/KEY: CDS
<222> LOCATION: (1520)..(1668)
<220> FEATURE:
<221> NAME/KEY: Intron
<222> LOCATION: (1669)..(1726)
<220> FEATURE:
<221> NAME/KEY: CDS
<222> LOCATION: (1727)..(1743)

<400> SEQUENCE: 7 atg aag tac gca act gcc tct ctc gtg gct gcg gcc act gtc tcc caa         48
Met Lys Tyr Ala Thr Ala Ser Leu Val Ala Ala Ala Thr Val Ser Gln
            -15                 -10                  -5 gtt gcg gcg gtatgtcttc agtctactat acattctgat ccttacttat                 97
Val Ala Ala
         -1 aggcaacata g gtg tac cag cag tgc ggc ggt atc ggc ttc g gttggtagca      149
             Val Tyr Gln Gln Cys Gly Gly Ile Gly Phe
              1               5                  10 gtgcaagtga cctatctaat tacccttgct aacgaccttg cag tt ggg ccc act         203
                                                   Val Gly Pro Thr gct tgc gat gct cag tcg gtg tgc act act atc aac gcc t gtatgtctag       253
Ala Cys Asp Ala Gln Ser Val Cys Thr Thr Ile Asn Ala
 15                  20                  25 cctgacatca ttataccgac ataaactgat gttggcatgc ag ac tac tcg cag          306
                                                  Tyr Tyr Ser Gln
                                                            30 tgc ctc ccg acg tcc tcc ccc tcc gcg ccc tcc gct ccc agc tcc ggc        354
Cys Leu Pro Thr Ser Ser Pro Ser Ala Pro Ser Ala Pro Ser Ser Gly
         35                  40                  45 ctg atc cag ctc ggt ggt gtc aac act gcg gga tac gac ttc agc gtt        402
Leu Ile Gln Leu Gly Gly Val Asn Thr Ala Gly Tyr Asp Phe Ser Val
     50                  55                  60 gtacgtcctc tgagagaatg tttccaaacg cattactcaa ggatattgac gtag gct        459
                                                              Ala act gat gga agc ttc acc ggc acc ggt gtc tct ccc ccg cca tcc cag        507
Thr Asp Gly Ser Phe Thr Gly Thr Gly Val Ser Pro Pro Pro Ser Gln
 65                  70                  75                  80 ttc acc cac ttc tcc agc cag ggt gct aac ctc tac cgc att c              550
Phe Thr His Phe Ser Ser Gln Gly Ala Asn Leu Tyr Arg Ile
                 85                  90 gtaagtgggc tcagcattgc gaagggaagt cgtactgact gtatgtttta ttgtag cc       608
                                                                Pro
                                                                 95 ttc g gtgtgccgtt tctctagcga tgtcgattgg tccaattgct gacccttcct tag       665
Phe ca tgg cag ctg atg acg ccc aac ctc ggc gga ccc atc aac gag acg        712
Ala Trp Gln Leu Met Thr Pro Asn Leu Gly Gly Pro Ile Asn Glu Thr
             100                 105                 110 ttc ttc tcc acc tac gac cag act gtc caa gcc gcg ctc aac tcg ggc        760
Phe Phe Ser Thr Tyr Asp Gln Thr Val Gln Ala Ala Leu Asn Ser Gly
         115                 120                 125 tca aac gtg cac gtc atc gtc gac ctg cac aac tac gcg cgc tgg aac        808
Ser Asn Val His Val Ile Val Asp Leu His Asn Tyr Ala Arg Trp Asn
 130                 135                 140
```

```
ggc ggt atc atc gcc cag ggc ggc ccg acc aac gag gag tac gcg tcc      856
Gly Gly Ile Ile Ala Gln Gly Gly Pro Thr Asn Glu Glu Tyr Ala Ser
145                 150                 155                 160 atc tgg acc cac ctc gcc gcc aag tac ggc tcc aac gag cgc atc att      904
Ile Trp Thr His Leu Ala Ala Lys Tyr Gly Ser Asn Glu Arg Ile Ile
            165                 170                 175 tt  gtacgcccgc ccctcggtct tctgatacgt tgaagaggag agctcacgac            956
Phe gtctgcctgc ag c ggt gtc atg aac gag ccg cac gac atc ccc aac gtc     1005
                Gly Val Met Asn Glu Pro His Asp Ile Pro Asn Val
                180                 185 cag acc tgg gtc gac tcc gtc cag ttc gtc gtc aac gct atc cgc cag     1053
Gln Thr Trp Val Asp Ser Val Gln Phe Val Val Asn Ala Ile Arg Gln
190                 195                 200                 205 gcc ggc gcg acg aac ttc ctc ctc ctg cct ggc tcc agc ttc tca tcc     1101
Ala Gly Ala Thr Asn Phe Leu Leu Leu Pro Gly Ser Ser Phe Ser Ser
                    210                 215                 220 gcc cag gcc ttc ccc acc gag gcc ggc cct tat ctc gtc aaa gta act     1149
Ala Gln Ala Phe Pro Thr Glu Ala Gly Pro Tyr Leu Val Lys Val Thr
                225                 230                 235 gac ccg ctt ggc ggc acc gac aag ctg atc ttc gat g gtaagcccag        1196
Asp Pro Leu Gly Gly Thr Asp Lys Leu Ile Phe Asp
240                 245 catcatagaa ctcattatgt acacaagtta acccgaccgc ag tc  cac aag tac      1249
                                                  Val His Lys Tyr
                                                  250 ctc gac agc gac aac agc ggc acc cac ccc gac tgc acc acc              1291
Leu Asp Ser Asp Asn Ser Gly Thr His Pro Asp Cys Thr Thr
    255                 260                 265 gtacgttgca cctcctaaac tatgcacacc tctccccgcg atgctcacgt acattccgca   1351 g gac aac gtg gac gtc ctt aag acc ctc gtc cag ttc ctt cag caa aac   1400
  Asp Asn Val Asp Val Leu Lys Thr Leu Val Gln Phe Leu Gln Gln Asn
      270                 275                 280 ggc aac cgt cag gcg atc ctg agc gag acc ggc gga ggc aac act gcg     1448
Gly Asn Arg Gln Ala Ile Leu Ser Glu Thr Gly Gly Gly Asn Thr Ala
                285                 290                 295 agc tgt gag act ct  gtaagtcgcg cacaccgctt acagtcttca agcattgcgc     1502
Ser Cys Glu Thr Leu
300 taatgcagcc cccgcag c ctc aac aac gag ctc tcg ttc gtc aag tcc gcg    1553
                    Leu Asn Asn Glu Leu Ser Phe Val Lys Ser Ala
                    305                 310                 315 ttc ccg acc ctc gcc ggc ttc tca gtc tgg gct gct ggc gcg ttc gac     1601
Phe Pro Thr Leu Ala Gly Phe Ser Val Trp Ala Ala Gly Ala Phe Asp
                320                 325                 330 acc acc tac gtg ctc acc gtc tcg ccc aac ccc gat ggc tcc gac cag    1649
Thr Thr Tyr Val Leu Thr Val Ser Pro Asn Pro Asp Gly Ser Asp Gln
                335                 340                 345 ccc ctc tgg aac gac gcc g gtacgtgtga tcccatgcat cccgtcctat          1698
Pro Leu Trp Asn Asp Ala
350 cgattcaatt gctcactgtt cgctacag tc  aag ccc aac ctg ccc tga          1746
                                   Val Lys Pro Asn Leu Pro
                                   355

<210> SEQ ID NO 8
<211> LENGTH: 378
<212> TYPE: PRT
<213> ORGANISM: Trametes versicolor
```

<400> SEQUENCE: 8

```
Met Lys Tyr Ala Thr Ala Ser Leu Val Ala Ala Thr Val Ser Gln
            -15                 -10                  -5
Val Ala Ala Val Tyr Gln Gln Cys Gly Gly Ile Gly Phe Val Gly Pro
         -1   1                  5                      10
Thr Ala Cys Asp Ala Gln Ser Val Cys Thr Thr Ile Asn Ala Tyr Tyr
     15              20                  25
Ser Gln Cys Leu Pro Thr Ser Ser Pro Ser Ala Pro Ser Ala Pro Ser
 30              35                  40                  45
Ser Gly Leu Ile Gln Leu Gly Gly Val Asn Thr Ala Gly Tyr Asp Phe
             50                  55                  60
Ser Val Ala Thr Asp Gly Ser Phe Thr Gly Thr Gly Val Ser Pro Pro
             65                  70                  75
Pro Ser Gln Phe Thr His Phe Ser Ser Gln Gly Ala Asn Leu Tyr Arg
             80                  85                  90
Ile Pro Phe Ala Trp Gln Leu Met Thr Pro Asn Leu Gly Gly Pro Ile
 95                 100                 105
Asn Glu Thr Phe Phe Ser Thr Tyr Asp Gln Thr Val Gln Ala Ala Leu
110                 115                 120                 125
Asn Ser Gly Ser Asn Val His Val Ile Val Asp Leu His Asn Tyr Ala
                130                 135                 140
Arg Trp Asn Gly Gly Ile Ile Ala Gln Gly Gly Pro Thr Asn Glu Glu
                145                 150                 155
Tyr Ala Ser Ile Trp Thr His Leu Ala Ala Lys Tyr Gly Ser Asn Glu
                160                 165                 170
Arg Ile Ile Phe Gly Val Met Asn Glu Pro His Asp Ile Pro Asn Val
                175                 180                 185
Gln Thr Trp Val Asp Ser Val Gln Phe Val Val Asn Ala Ile Arg Gln
190                 195                 200                 205
Ala Gly Ala Thr Asn Phe Leu Leu Leu Pro Gly Ser Ser Phe Ser Ser
                210                 215                 220
Ala Gln Ala Phe Pro Thr Glu Ala Gly Pro Tyr Leu Val Lys Val Thr
                225                 230                 235
Asp Pro Leu Gly Gly Thr Asp Lys Leu Ile Phe Asp Val His Lys Tyr
                240                 245                 250
Leu Asp Ser Asp Asn Ser Gly Thr His Pro Asp Cys Thr Thr Asp Asn
255                 260                 265
Val Asp Val Leu Lys Thr Leu Val Gln Phe Leu Gln Asn Gly Asn
270                 275                 280                 285
Arg Gln Ala Ile Leu Ser Glu Thr Gly Gly Gly Asn Thr Ala Ser Cys
                290                 295                 300
Glu Thr Leu Leu Asn Asn Glu Leu Ser Phe Val Lys Ser Ala Phe Pro
                305                 310                 315
Thr Leu Ala Gly Phe Ser Val Trp Ala Ala Gly Ala Phe Asp Thr Thr
                320                 325                 330
Tyr Val Leu Thr Val Ser Pro Asn Pro Asp Gly Ser Asp Gln Pro Leu
                335                 340                 345
Trp Asn Asp Ala Val Lys Pro Asn Leu Pro
350                 355
```

POLYPEPTIDES HAVING ENDOGLUCANSE ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

BACKGROUND OF THE INVENTION

1. Field of the Invention

The present invention relates to polypeptides having endoglucanase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is undesirable for ethanol production.

The present invention provides polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide having at least 78% sequence identity to the mature polypeptide of SEQ ID NO: 2, a polypeptide having at least 94% sequence identity to the mature polypeptide of SEQ ID NO: 4, a polypeptide having at least 76% sequence identity to the mature polypeptide of SEQ ID NO: 6, or a polypeptide having at least 81% sequence identity to the mature polypeptide of SEQ ID NO: 8;

(b) a polypeptide encoded by a polynucleotide that hybridizes under low, or medium, or medium-high, or high, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 3, SEQ ID NO: 5, or SEQ ID NO: 7; or the cDNA sequence thereof;

(d) a variant of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions; and (e) a fragment of the polypeptide of (a), (b), (c), or (d) that has endoglucanase activity.

The present invention also relates to isolated polypeptides comprising a catalytic domain selected from the group consisting of:

(a) a catalytic domain having at least 60% sequence identity to the catalytic domain of SEQ ID NO: 2 (for example, amino acids 92 to 419 of SEQ ID NO: 2), SEQ ID NO: 4 (for example, amino acids 73 to 386 of SEQ ID NO: 4), SEQ ID NO: 6 (for example, amino acids 67 to 378 of SEQ ID NO: 6), or SEQ ID NO: 8 (for example, amino acids 67 to 378 of SEQ ID NO: 8);

(b) a catalytic domain encoded by a polynucleotide having at least 60% sequence identity to the catalytic domain coding sequence of SEQ ID NO: 1 (for example, nucleotides 459-564, 621-838, 896-993, 1050-1133, 1184-1345, 1410-1585, and 1639-1778 of SEQ ID NO: 1), SEQ ID NO: 3 (for example, nucleotides 334-459, 532-700, 760-808, 862-872, 931-956, 1019-1093, 1156-1312, 1384-1640, and 1711-1782 of SEQ ID NO: 3), SEQ ID NO: 5 (for example, nucleotides 361-408, 463-556, 613-618, 669-909, 975-1192, 1245-1297, 1362-1471, 1540-1688, and 1753-1769 of SEQ ID NO: 5), or SEQ ID NO: 7 (for example, nucleotides 355-402, 457-550, 607-612, 666-906, 969-1186, 1239-1291, 1353-1462, 1520-1668, and 1727-1743 of SEQ ID NO: 7);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, or SEQ ID NO: 8; and (d) a fragment of a catalytic domain of (a), (b), or (c), which has endoglucanase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading a cellulosic material, comprising: treating the cellulosic material with an enzyme composition in the presence of a polypeptide having endoglucanase activity of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a polypeptide having endoglucanase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having endoglucanase activity of the present invention. In one aspect, the fermenting of the cellulosic material produces a fermentation product. In another aspect, the processes further comprise recovering the fermentation product from the fermentation.

The present invention also relates to a polynucleotide encoding a signal peptide comprising or consisting of amino acids 1 to 21 of SEQ ID NO: 2, amino acids 1 to 20 of SEQ ID NO: 4, amino acids 1 to 19 of SEQ ID NO: 6, or amino acids 1 to 19 of SEQ ID NO: 8, which is operably linked to a gene encoding a protein; nucleic acid constructs, expression vectors, and recombinant host cells comprising the polynucleotides; and methods of producing a protein.

-continued

| | |
|---|---|
| Exon 6 | 896-993 bp |
| Intron 6 | 994-1049 bp |
| Exon 7 | 1050-1133 bp |
| Intron 7 | 1134-1183 bp |
| Exon 8 | 1184-1345 bp |
| Intron 8 | 1346-1409 bp |
| Exon 9 | 1410-1585 bp |
| Intron 9 | 1586-1638 bp |
| Exon 10 | 1639-1781 bp |

Sequences of the Invention

Trametes versicolor Strain NN055586_Genomic Nucleotide Sequence (SEQ ID NO: 1):

```
   1  ATGAAGACTT TCGCAGCCTT GCTTTCCGCT GTCACTCTCG CGCTCTCGGT GCGCGCCCAG GCGGCTGTCT GGAGTCAATG
  81  TAAGTGCCGC TGCTTTTCAT TGATACGAGA CTCTACGCCG AGCTGACGTG CTACCGTATA GGTGGCGGTA CAGTAAGTTA
 161  TCATAGCATA CCGCCTACAT GCACAAGGAC ATACTGCTGA TCAATTCTCT GTGCAGGGTT GGACGGGCGA GACCACTTGC
 241  GTTGCTGGTT CGGTTTGTAC CTCCTTGAGC TCATGTGAGC GACTTTCAAT CCGTCGTCAT TGCTCCTCAT GTATTGACGA
 321  TTGGCCTTCA TAGCATACTC TCAATGCGTT CCGGGCTCCG CAACGTCCAG CGCTCCGGCG GCCCCCTCAG CGACAACTTC
 401  AGGCCCCGCA CCTCCAGCAT CCACGTGTGC ACCCAACAGC CCGCCCGCGA GCGCAGGCAA ACTGCGCTTC GCGGGTGTCA
 481  ACATCTCCGG TTTCGACTTC GGATGCAGCA CGGACGGAAC GTGCTCGGCC AGCGGGGCAT GGCCGCCATT GACCAAGTAC
 561  TACGGTCAGC CCCTTTCCTG CAGGGTAGTG GCGAGGGTGT TGACATTTTT TGGACGACAG GCATGGATGG TGCGGGCCAG
 641  ATGAAGCACT TTGTCGAGAA CGACGGCTAC AATGTTTTCC GCCTGCCCGT TGGGTGGCAG TTCCTGACGA ACGGTGCCGC
 721  CACTGGTGAC ATAGACGAGG TCAACTTCGC CGAGTACGAT GATCTCGTCC AAGCGTGCCT CGACGCAGGC GCGTCGTGCA
 801  TCGTTGAGGT TCACAACTAC GCGCGGTTTA ACGGCAAGGT ACGATGCGCA CTTCTGCGAG CCAGCTGACT GTAGCCAACC
 881  AAACCTGGCA TACAGATCAT CGGTCAGGGT GGGCCCGCAA ATGACCAGTT CGCCGCCCTT TGGAGCAGTT TTGCCTCCAA
 961  GTACGCCGAC AACGACAAGA TCATCTTTGG GATGTCAGTG CCTTTTCCGG ATTCCGCAAA CTGTAGCTCA TGCAATAACC
1041  GACTCACAGT ATGAACGAAC CACATGACGT CCCCGATATC AACCTCTGGG CGGAGAGTGT CCAGGCAGCA GTGACCGCCA
1121  TCCGCCAGGC CGGGTATGCA TGTCAACCCC AAAACCAAAT GCTGCTCACT AATCGGTCCC TAGTGCGACT TCGCAGCTGA
1201  TCCTGCTCCC GGGCAACAAC TGGACGTCTG CGGAGACCTT CGTCTCCAAC GGCTCGGCCG ATGCGCTCAA CAAGGTCACG
1281  AACCCCGACG GCAGCATCAC GAACCTCATC TTCGACGTGC ACAAGTACCT CGACTTCGAC AACTCGTACG TCTATGCCCA
1361  CTTGCCCCGT TGATTCTGCA GGTGAATTGA CGTAATGCGG ATCGCACAGG GGCACGAACG CAGAGTGCAC GACGAACAAC
1441  ATCGACAACG CGTGGGCGCC GCTCGCGCAG TGGCTGCGCT GCAACGGCCG GCAGGCGTTC AACACCGAGA CGGGCGGCGG
1521  GAACGTCGCG TCGTGCGAGA CGTTCATGTG CGAGCAGGTC GCGTTCCAGA CGGCGAACTC GGACGGTGCG TTCTGCGTCC
1601  TCGCGTCGTT CTTCACTCTC GCTGATGATA TCGTGTAGTG TTCTTGGGCT ATGTCGGCTG GGCGGCGGGC AACTTCTACG
1681  AAGGCTACGT GCTGAGCGAG GTCCCGACCC AGAATGCGGA TGGGAGCTGG ACGGACCAGC CGCTTGTTGC GCAGTGCATG
1761  GCGCCCAACG CTTCTCAGTG A
```

Exons/Introns (in Base Pairs) of SEQ ID NO: 1:

| | |
|---|---|
| Exon 1 | 1-79 bp |
| Intron 1 | 80-141 bp |
| Exon 2 | 142-152 bp |
| Intron 2 | 153-216 bp |
| Exon 3 | 217-274 bp |
| Intron 3 | 275-333 bp |
| Exon 4 | 334-564 bp |
| Intron 4 | 565-620 bp |
| Exon 5 | 621-838 bp |
| Intron 5 | 839-895 bp |

Features (in Base Pairs) of SEQ ID NO: 1:

| | |
|---|---|
| Signal Peptide | 1-63 bp |
| Cellulose Binding Module (CBM 1) | 64-79, 142-152, 217-274, 334-353 bp |
| Linker | 354-458 bp |
| Endoglucanase catalytic site | 459-564, 621-838, 896-993, 1050-1133, 1184-1345, 1410-1585, 1639-1778 bp |
| Stop codon | 1779-1781 bp |

Protein Sequence of Trametes versicolor Strain NN055586_protein
(SEQ ID NO: 2):

| | |
|---|---|
| 1 | MKTFAALLSA VTLALSVRAQ AAVWSQCGGT GWTGETTCVA GSVCTSLSSS YSQCVPGSAT |
| 61 | SSAPAAPSAT TSGPAPPAST CAPNSPPASA GKLRFAGVNI SGFDFGCSTD GTCSASGAWP |
| 121 | PLTKYYGMDG AGQMKHFVEN DGYNVFRLPV GWQFLTNGAA TGDIDEVNFA EYDDLVQACL |
| 181 | DAGASCIVEV HNYARFNGKI IGQGGPANDQ FAALWSSFAS KYADNDKIIF GIMNEPHDVP |
| 241 | DINLWAESVQ AAVTAIRQAG ATSQLILLPG NNWTSAETFV SNGSADALNK VTNPDGSITN |
| 301 | LIFDVHKYLD FDNSGTNAEC TTNNIDNAWA PLAQWLRCNG RQAFNTETGG GNVASCETFM |
| 361 | CEQVAFQTAN SDVFLGYVGW AAGNFYEGYV LSEVPTQNAD GSWTDQPLVA QCMAPNASQ |

Features of SEQ ID NO: 2 (Amino Acid Positions):

| | |
|---|---|
| Signal Peptide | 1-21 |
| Cellulose Binding Module (CBM 1) | 22-56 |
| Linker | 57-91 |
| Endoglucanase catalytic site | 92-419 |

Signal Peptide Sequence of SEQ ID NO: 2:

MKTFAALLSAVTLALSVRAQA

Trametes versicolor Strain NN055586 Genomic Nucleotide Sequence (SEQ ID NO: 3):

| | |
|---|---|
| 1 | ATGAAGACGG TTATCCTCTC CCTCGCTGCC GCGCTCTTCA GCGCCGCGCC CGTGCTCTCC ACCGCCGTCT GGGGCCAGTG |
| 81 | CGGCGTGAGT ACTCGACTCG CGACGCGGTC ACGGGGCCAT ACTCACCATC TGCTCGTGTT CTAGGGCACT GGCTTCTCTG |
| 161 | GCGACACGAC CTGCGCCTCC GGCTCTAGCT GCGTCGTAGT CAACCAATGT ATGCCGTCCA CGTCCACCCG CTGACATCCT |
| 241 | TTACTGACCA CTCACCCTTG AACAGACTAC TCGCAATGCC AGCCCGGCGC GTCCGCCCCC ACGTCGACTG CCTCGGCCCC |
| 321 | CGGCCCTTCC GGCTGCTCGG GCACGCGCAC CAAGTTCAAG CTCTTCGGTG TGAACGAGTC CGGCGCGGAG TTCGGGAACA |
| 401 | CCGTCATCCC GGGCGCGCTC GGCACGGACT ACACCTGGCC GTCGCCCACC TCCATCGACG TGCGTACTGT TGTCGGACAT |
| 481 | GTCTGACGTA GAAGCAGAGG ATGCTGATGG ATGGACGGTT GGGCGATGCA GTTCTTCCTC GGGCAGGGCT TCAACACCTT |
| 561 | CCGCATCCCG TTCCTGATGG AGCGCGTCAG CCCGCCGTCG ACGGGCGGCC TTACTGGCCC GTTCAACAGC ACGTACCTCG |
| 641 | ACGGGCTGAA GCAGACTGTT AGCTACATCA CGGGCAAGGG GGGCTTTGCC ATCGTCGACC GTGAGTGCTT ACTCCCAACG |
| 721 | TATGCTATTT GGAGAGTGGA GTACTGATCT GGTGTGCAGC GCACAACTTC ATGATCTTCA CGGCGCGAC GATCACGAGC |
| 801 | ACCAGCCAGT AAGTCGCATT ATTTACGGTG GAAGAGTTTT ACTGATATCT ATCGCGTTTA GGTTCCAGGC TTGTACGTAT |
| 881 | TCGCGTCGCC ATATACACGA CACCGAGCTC TTTGCTGATG TTGACGACAG GGTGGCAGAA GCTCGCTGCT GAGTTCGTGA |
| 961 | GTGTGCTCCA TGGCTACGCG GCCGTGAACG CTCTGGCTGA CAAGATGCCG CCTCCCAGAA AACCGACAAC AACGTCATCT |
| 1041 | TCGACCTGAT GAACGAGCCG CACGACATCC CCGCGCAGAC CGTCTTCCAG CTCGTACGTA ACACTTTCCG TATGTCCCAA |
| 1121 | GCAACCATGT GTTAAGTGAT CATGATCCCG CGCAGATGCA AGCGGCCGTG AACGGCGTGC GCGCGAGCGG CGCGACGAGC |
| 1201 | CAGCTCATCC TCGCCGAGGG CACGAGCTGG ACCGGCGCGT GGACCTGGAC GACGTCGGGC AACAGCGACG CGTTCGGCGC |
| 1281 | GATCAAGGAC CCCAACAACA ACATCGCCAT CCGTGCGTCC CCCCCTCCC CCTTCCTCTT GCCCCTGCC TACTGACGAA |
| 1361 | CACGCCATGG GATTGACACA CAGAGATGCA CCAGTACCTA GACTCGGACG GGTCGGGGAC GTCCCGATC TGCGTGTCGG |
| 1441 | ACACGATCGG GGCGGAGCGG CTGCAGGCGG CGACGCAGTG GCTGCAGCAG ACGGGCCTCA AGGGCTTCCT CGGCGAGATC |
| 1521 | GGGACGGGGA ACAACACGCA GTGCGTGACC GCGCTGCAGG GCGCGCTGTG CGAGATGCAG CAGGCGGGCG GACGTGGCT |
| 1601 | CGGCGCGCTC TGGTGGGCGG CGGGGCCGTG GTGGGGAGAC GTGAGTGGCT TTCTGTGCTT ATGTGGGGGA GGGGAGTGG |
| 1681 | GGGCTGACGG TGGTTGTGTT GGACTTGCAG TACTACCAGA GCATCGAGCC CCCGAACGGG GACGCGATCG CTGCGATCCT |
| 1761 | CCCGGCGCTC AAGGCGTTCC AGTAG |

Exons/Introns (in Base Pairs) of SEQ ID NO: 3:

| | |
|---|---|
| Exon 1 | 1-84 bp |
| Intron 1 | 85-144 bp |
| Exon 2 | 145-208 bp |
| Intron 2 | 209-265 bp |
| Exon 3 | 266-459 bp |
| Intron 3 | 460-531 bp |
| Exon 4 | 532-700 bp |
| Intron 4 | 701-759 bp |
| Exon 5 | 760-808 bp |
| Intron 5 | 809-861 bp |
| Exon 6 | 862-872 bp |
| Intron 6 | 873-930 bp |
| Exon 7 | 931-956 bp |
| Intron 7 | 957-1018 bp |
| Exon 8 | 1019-1093 bp |
| Intron 8 | 1094-1155 bp |
| Exon 9 | 1156-1312 bp |
| Intron 9 | 1313-1383 bp |
| Exon 10 | 1384-1640 bp |
| Intron 10 | 1641-1710 bp |
| Exon 11 | 1711-1785 bp |

Features (in Base Pairs) of SEQ ID NO: 3:

| | |
|---|---|
| Signal Peptide | 1-60 bp |
| Cellulose Binding Module (CBM 1) | 61-84, 145-208, 266-285 bp |
| Linker | 286-333 bp |
| Endoglucanase catalytic site | 334-459, 532-700, 760-808, 862-872, 931-956, 1019-1093, 1156-1312, 1384-1640, 1711-1782 bp |
| Stop codon | 1783-1785 bp |

Protein Sequence of Trametes versicolor Strain NN055586_protein (SEQ ID NO: 4):

```
  1  MKTVILSLAA ALFSAAPVLS TAVWGQCGGT GFSGDTTCAS GSSCVVVNQY YSQCQPGASA
 61  PTSTASAPGP SGCSGTRTKF KLFGVNESGA EFGNTVIPGA LGTDYTWPSP TSIDFFLGQG
121  FNTFRIPFLM ERVSPPSTGG LTGPFNSTYL DGLKQTVSYI TGKGGFAIVD PHNFMIFNGA
181  TITSTSQFQA WWQKLAAEFK TDNNVIFDLM NEPHDIPAQT VFQLMQAAVN GVRASGATSQ
241  LILAEGTSWT GAWTWTTSGN SDAFGAIKDP NNNIAIQMHQ YLDSDGSGTS PICVSDTIGA
301  ERLQAATQWL QQTGLKGFLG EIGTGNNTQC VTALQGALCE MQQAGGTWLG ALWWAAGPWW
361  GDYYQSIEPP NGDAIAAILP ALKAFQ
```

Features of SEQ ID NO: 4 (Amino Acid Positions):

| | |
|---|---|
| Signal Peptide | 1-20 |
| Cellulose Binding Module (CBM 1) | 21-57 |
| Linker | 58-72 |
| Endoglucanase catalytic site | 73-386 |

Signal Peptide Sequence of SEQ ID NO: 4:

MKTVILSLAAALFSAAPVLS

Trametes versicolor Strain NN055586_Genomic Nucleotide Sequence (SEQ ID NO: 5):

```
   1  ATGAAGTACG CAACTGCCTC TCTCGTGGCT GCGGCCACCG TCTCCCAGGT TATGGCGGTA TGCACTCAGG CTAGTACTTC
  81  ACATGCTGGA TTATACTCAT TAGCAACGTA GGTGTACCAA CAGTGCGGTG GTATCGGTTT CGGTTAGCAG AATTGCAAGT
 161  GGCGCATTTG ACTGCCCTTG CTAACGAACT TGCAGATAGG CCCACTGCTT GTGATGCTCA CTCGGTGTGC ACTGCTATCA
 241  ATCCCCGTAT GTCTGTCCTG CTATCATTAC ACAGACATAG TAGGCTCATG CTGGCATGCA GACTACTCCC AGTGCCTCCC
 321  GTCGTCTTCC CCCTCGGCGC CCTCTGCCCC CCGCTCCAGC CTGATCCAGC TCGGTGGTGT CAACACTGCG GGATACGACT
 401  TCAGCGTTGT ACGTCCTCTG AAACAAAAGT CTTAGACCCA TTGCTCACAG ATATTGACAT AGACTATTGA CGGAAGCTTC
 481  ACCGGCACCG TGTCTCTCC CCCGCCCTCT CAGTATACCC ACTTCTCTAG CCAGGGTGCC AACCTCTTCC GCATTCGTGA
 561  GTGTGCCAAG TGTTGAGTAC GGGAATAATA CTGATCATAT TTTTTGCCGT AGCCTTCGGT GCGTTCTCTG TCTAGCGATG
 641  TGGTTTCGTT CTCATAGCCC TCCTTTAGCC TGGCAGCTGA TGACGCCGAA CGTCGGCGGA CCCATCAACG AGACGTTCTT
 721  CGCCACCTAT GACAAGACCG TCCAGGCTGC GCTCAACTCG GCTCCAACG TGCACGTCAT CATCGATCTG CACAACTATG
 801  CGCGCTGGAA CGGCGCCATC ATCGCTCAAG GCGGCCCGAC CAACGAGCAA TTTGCTTCCA TCTGGACCCA GCTCGCCGCC
 881  AAGTACGGCC GCAACAAGCG TATCATCTTG TACGCTCCTT CCTCCCTCTC TTTCTTATGA CATGTATGAG GATAGCTGCT
 961  GACGACGTCC GCAGCGGTCT CATGAACGAG CCACACGACC TCCCCAGCGT CCCGACCTGG GTTAAGTCTG TCCAGTTCGT
1041  TGTCAACGCC ATCCGCCATG CCGGCGCGAC GAACTTCCTC CTCCTGCCTG GCTCCAGCTT CTCATCCGCC CAGGCCTTCC
1121  CCACCGAGGC CGGCCCTGAC CTCGTCAAGG TCACTGACCC GCTCGGCGGC ACCCACAAGC TGATCTTCGA TGGTAGGTTT
1201  AGCGTGTTAG AACCCATCCT GTGCCGGACT GACCTCTGCC GCAGTCCACA GTATCTCGA CAGCGACAAC AGCGGCACTC
1281  ACCCCGACTG CACCACTGTA CGTTGCACCG CCCCGTCTAT CACGAACGCG ACTTCCAGCG ATGCTCATGC ACATTCCATA
1361  GGACAACGTC GACGTGCTGA AGACGCTCGT CCAGTTCCTC AAGCAGAACG GCAACCGCCA GGCGCTCCTC AGCGAGACCG
1441  GCGGAGGAAA CACCACGAGC TGCGAGACTC TGTAAGTGCC AGTGGCTTG CACGCCGCCC ACTTGGGCTT GTAGTAGCAC
1521  GCTGACGCAC TCCCCGAAGC CTCAACACCG AGCTCTCGTT CGTCAAGTCC GCGTTCCCGA CCCTCGTCGG CTTCTCCGCC
1601  TGGGCCGCCG GCGCGTTCGA CACCAACTAC GTGCTCACGC TCACGCCCAA CGCCGACGGC TCCGACCAGC CCTCTGGAT
1681  CGACGCCGGT ACGTGTGGCC CTGCCAGTGC TCATTCTGTC CTCTCGATAT AGGTGCTCAC CATTCGCTGC AGTCAAGCCC
1761  AACCTGCCTT GA
```

Exons/Introns (in Base Pairs) of SEQ ID NO: 5:

| | |
|---|---|
| Exon 1 | 1-57 bp |
| Intron 1 | 58-111 bp |
| Exon 2 | 112-142 bp |
| Intron 2 | 143-195 bp |
| Exon 3 | 196-246 bp |
| Intron 3 | 247-301 bp |
| Exon 4 | 302-408 bp |
| Intron 4 | 409-462 bp |
| Exon 5 | 463-556 bp |
| Intron 5 | 557-612 bp |
| Exon 6 | 613-618 bp |
| Intron 6 | 619-668 bp |
| Exon 7 | 669-909 bp |
| Intron 7 | 910-974 bp |
| Exon 8 | 975-1192 bp |
| Intron 8 | 1193-1244 bp |
| Exon 9 | 1245-1297 bp |
| Intron 9 | 1298-1361 bp |
| Exon 10 | 1362-1471 bp |
| Intron 10 | 1472-1539 bp |
| Exon 11 | 1540-1688 bp |
| Intron 11 | 1689-1752 bp |
| Exon 12 | 1753-1772 bp |

Features (in Base Pairs) of SEQ ID NO: 5:

| | |
|---|---|
| Signal Peptide | 1-57 bp |
| Cellulose Binding Module (CBM 1) | 112-142, 196-246, 302-321 bp |
| Linker | 322-360 bp |
| Endoglucanase catalytic site | 361-408, 463-556, 613-618, 669-909, 975-1192, 1245-1297, 1362-1471, 1540-1688, 1753-1769 bp |
| Stop codon | 1770-1772 bp |

Protein Sequence of Trametes versicolor Strain NN055586_protein
(SEQ ID NO: 6):

```
  1  MKYATASLVA AATVSQVMAV YQQCGGIGFD RPTACDAHSV CTAINPHYSQ CLPSSSPSAP
 61  SAPRSSLIQL GGVNTAGYDF SVTIDGSFTG TGVSPPPSQY THFSSQGANL FRIPFAWQLM
121  TPNVGGPINE TFFATYDKTV QAALNSGSNV HVIIDLHNYA RWNGAIIAQG GPTNEQFASI
181  WTQLAAKYGR NKRIIFGLMN EPHDLPSVPT WVKSVQFVVN AIRHAGATNF LLLPGSSFSS
241  AQAFPTEAGP DLVKVTDPLG GTHKLIFDVH KYLDSDNSGT HPDCTTDNVD VLKTLVQFLK
301  QNGNRQALLS ETGGGNTTSC ETLLNTELSF VKSAFPTLVG FSAWAAGAFD TNYVLTLTPN
361  ADGSDQPLWI DAVKPNLP
```

Features of SEQ ID NO: 6 (Amino Acid Positions):

| | |
|---|---|
| Signal Peptide | 1-19 |
| Cellulose Binding Module (CBM 1) | 20-53 |
| Linker | 54-66 |
| Endoglucanase catalytic site | 67-378 |

Signal Peptide Sequence of SEQ ID NO: 6:

MKYATASLVAAATVSQVMA

Trametes versicolor Strain NN055586_Genomic Nucleotide Sequence (SEQ ID NO: 7):

```
   1  ATGAAGTACG CAACTGCCTC TCTCGTGGCT GCGGCCACTG TCTCCCAAGT TGCGGCGGTA TGTCTTCAGT CTACTATACA
  81  TTCTGATCCT TACTTATAGG CAACATAGGT GTACCAGCAG TGCGGCGGTA TCGGCTTCGG TTGGTAGCAG TGCAAGTGAC
 161  CTATCTAATT ACCCTTGCTA ACGACCTTGC AGTTGGGCCC ACTGCTTGCG ATGCTCAGTC GGTGTGCACT ACTATCAACG
 241  CCTGTATGTC TAGCCTGACA TCATTATACC GACATAAACT GATGTTGGCA TGCAGACTAC TCGCAGTGCC TCCCGACGTC
 321  CTCCCCCTCC GCGCCCTCCG CTCCCAGCTC CGGCCTGATC CAGCTCGGTG GTGTCAACAC TGCGGGATAC GACTTCAGCG
 401  TTGTACGTCC TCTGAGAGAA TGTTTCCAAA CGCATTACTC AAGGATATTG ACGTAGGCTA CTGATGGAAG CTTCACCGGC
 481  ACCGGTGTCT CTCCCCCGCC ATCCCAGTTC ACCCACTTCT CCAGCCAGGG TGCTAACCTC TACCGCATTC GTAAGTGGGC
 561  TCAGCATTGC GAAGGGAAGT CGTACTGACT GTATGTTTTA TTGTAGCCTT CGGTGTGCCG TTTCTCTAGC GATGTCGATT
 641  GGTCCAATTG CTGACCCTTC CTTAGCATGG CAGCTGATGA CGCCCAACCT CGGCGGACCC ATCAACGAGA CGTTCTTCTC
 721  CACCTACGAC CAGACTGTCC AAGCCGCGCT CAACTCGGGC TCAAACGTGC ACGTCATCGT CGACCTGCAC AACTACGCGC
 801  GCTGGAACGG CGGTATCATC GCCCAGGGCG GCCCGACCAA CGAGGAGTAC GCGTCCATCT GGACCCACCT CGCCGCCAAG
 881  TACGGCTCCA ACGAGCGCAT CATTTTGTAC GCCCGCCCCT CGGTCTTCTG ATACGTTGAA GAGGAGAGCT CACGACGTCT
 961  GCCTGCAGCG GTGTCATGAA CGAGCCGCAC GACATCCCCA CGTCCAGAC CTGGGTCGAC TCCGTCCAGT TCGTCGTCAA
1041  CGCTATCCGC CAGGCCGGCG CGACGAACTT CCTCCTCCTG CCTGGCTCCA GCTTCTCATC CGCCCAGGCC TTCCCCACCG
1121  AGGCCGGCCC TTATCTCGTC AAAGTAACTG ACCCGCTTGG CGGCACCGAC AAGCTGATCT TCGATGGTAA GCCCAGCATC
1201  ATAGAACTCA TTATGTACAC AAGTTAACCC GACCGCAGTC CACAAGTACC TCGACAGCGA CAACAGCGGC ACCCACCCCG
1281  ACTGCACCAC CGTACGTTGC ACCTCCTAAA CTATGCACAC CTCTCCCCGC GATGCTCACG TACATTCCGC AGGACAACGT
1361  GGACGTCCTT AAGACCCTCG TCCAGTTCCT TCAGCAAAAC GGCAACCGTC AGGCGATCCT GAGCGAGACC GGCGGAGGCA
1441  ACACTGCGAG CTGTGAGACT CTGTAAGTCG CGCACACCGC TTACAGTCTT CAAGCATTGC GCTAATGCAG CCCCCGCAGC
1521  CTCAACAACG AGCTCTCGTT CGTCAAGTCC GCGTTCCCGA CCCTCGCCGG CTTCTCAGTC TGGGCTGCTG GCGCGTTCGA
1601  CACCACCTAC GTGCTCACCG TCTCGCCCAA CCCCGATGGC TCCGACCAGC CCCTCTGGAA CGACGCCGGT ACGTGTGATC
1681  CCATGCATCC CGTCCTATCG ATTCAATTGC TCACTGTTCG CTACAGTCAA GCCCAACCTG CCCTGA
```

Exons/Introns (in Base Pairs) of SEQ ID NO: 7:

| | |
|---|---|
| Exon 1 | 1-57 bp |
| Intron 1 | 58-108 bp |
| Exon 2 | 109-139 bp |
| Intron 2 | 140-192 bp |
| Exon 3 | 193-243 bp |
| Intron 3 | 244-295 bp |
| Exon 4 | 296-402 bp |
| Intron 4 | 403-456 bp |
| Exon 5 | 457-550 bp |
| Intron 5 | 551-606 bp |
| Exon 6 | 607-612 bp |
| Intron 6 | 613-665 bp |
| Exon 7 | 666-906 bp |
| Intron 7 | 907-968 bp |
| Exon 8 | 969-1186 bp |
| Intron 8 | 1187-1238 bp |
| Exon 9 | 1239-1291 bp |
| Intron 9 | 1292-1352 bp |
| Exon 10 | 1353-1462 bp |
| Intron 10 | 1463-1519 bp |
| Exon 11 | 1520-1668 bp |
| Intron 11 | 1669-1726 bp |
| Exon 12 | 1727-1746 bp |

Features (in Base Pairs) of SEQ ID NO: 7:

| | |
|---|---|
| Signal Peptide | 1-57 bp |
| Cellulose Binding Module (CBM 1) | 109-139, 193-243, 296-315 bp |
| Linker | 316-354 bp |
| Endoglucanase catalytic site | 355-402, 457-550, 607-612, 666-906, 969-1186, 1239-1291, 1353-1462, 1520-1668, 1727-1743 bp |
| Stop codon | 1744-1746 bp |

```
Protein Sequence of Trametes versicolor Strain NN055586_protein
                        (SEQ ID NO: 8):

1  MKYATASLVA AATVSQVAAV YQQCGGIGFV GPTACDAQSV CTTINAYYSQ CLPTSSPSAP

61  SAPSSGLIQL GGVNTAGYDF SVATDGSFTG TGVSPPPSQF THFSSQGANL YRIPFAWQLM

121  TPNLGGPINE TFFSTYDQTV QAALNSGSNV HVIVDLHNYA RWNGGIIAQG GPTNEEYASI

181  WTHLAAKYGS NERIIFGVMN EPHDIPNVQT WVDSVQFVVN AIRQAGATNF LLLPGSSFSS

241  AQAFPTEAGP YLVKVTDPLG GTDKLIFDVH KYLDSDNSGT HPDCTTDNVD VLKTLVQFLQ

301  QNGNRQAILS ETGGGNTASC ETLLNNELSF VKSAFPTLAG FSVWAAGAFD TTYVLTVSPN

361  PDGSDQPLWN DAVKPNLP
```

Features of SEQ ID NO: 8 (Amino Acid Positions):

| | |
|---|---|
| Signal Peptide | 1-19 |
| Cellulose Binding Module (CBM 1) | 20-53 |
| Linker | 54-66 |
| Endoglucanase catalytic site | 67-378 |

Signal Peptide Sequence of SEQ ID NO: 8:

MKYATASLVAAATVSQVAA

DEFINITIONS

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

In one aspect, the polypeptides of the present invention have at least 20%, e.g., at least 40%, at least 50%, at least 60%, at least 70%, at least 80%, at least 90%, at least 95%, or at least 100% of the endoglucanase activity of the mature polypeptide of SEQ ID NO: 2, SEQ ID NO: 4, SEQ ID NO: 6, or SEQ ID NO: 8.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 micromole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 microliters for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 micromole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 micromole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 micromole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 micromole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has endoglucanase activity. In one aspect, a fragment contains at least 20 amino acid residues, e.g., at least 30 to 418 amino acid residues or at least 50 to 400, 80 to 360, 100 to 340, 150 to 300, or 200 to 250, or any number in between, amino acid residues of SEQ ID NO: 2. In another aspect, a fragment contains at least 20 amino acid residues, e.g., at least 30 to 385 amino acid residues or at least 50 to 370, 80 to 350, 100 to 330, 150 to 300, or 200 to 250, or any number in between, amino acid residues of SEQ ID NO: 4. In another aspect, a fragment contains at least 20 amino acid residues, e.g., at least 30 to 386 amino acid residues or at least 50 to 380, 80 to 360, 100 to 330, 150 to 300, or 200 to 250, or any number in between, amino acid residues of SEQ ID NO: 6. In another aspect, a fragment contains at least 20 amino acid residues, e.g., at least 30 to 377 amino acid residues or at least 50 to 370, 80 to 350, 100 to 330, 150 to 300, or 200 to 250, or any number in between, amino acid residues of SEQ ID NO: 8.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 419 of SEQ ID NO: 2 based on the SignalP program (Nielsen et al., 1997, *Protein Engineering* 10:1-6) that predicts amino acids 1 to 21 of SEQ ID NO: 2 are a signal peptide. In another aspect, the mature polypeptide is amino acids 1 to 419 of SEQ ID NO: 2. In another aspect, the mature polypeptide is amino acids 21 to 386 of SEQ ID NO: 4 based on the SignalP program that predicts amino acids 1 to 20 of SEQ ID NO: 4 are a signal peptide. In another aspect, the mature polypeptide is amino acids 1 to 386 of SEQ ID NO: 4. In another aspect, the mature polypeptide is amino acids 20 to 378 of SEQ ID NO: 6 based on the SignalP program that predicts amino acids 1 to 19 of SEQ ID NO: 6 are a signal peptide. In another aspect, the mature polypeptide is amino acids 1 to 378 of SEQ ID NO: 6. In another aspect, the mature polypeptide is amino acids 20 to 378 of SEQ ID NO: 8 based on the SignalP program that predicts amino acids 1 to 19 of SEQ ID NO: 8 are a signal peptide. In another aspect, the mature polypeptide is amino acids 1 to 378 of SEQ ID NO: 8. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having endoglucanase activity. In one aspect, the mature polypeptide coding sequence is nucleotides 64 to 1778 of SEQ ID NO: 1 or the cDNA sequence thereof based on the SignalP program (Nielsen et al., 1997, supra) that predicts nucleotides 1 to 63 of SEQ ID NO: 1 encode a signal peptide. In another aspect, the mature polypeptide coding sequence is nucleotides 1 to 1778 of SEQ ID NO: 1 or the cDNA sequence thereof. In another aspect, the mature polypeptide coding sequence is nucleotides 61 to 1782 of SEQ ID NO: 3 or the cDNA sequence thereof based on the SignalP program that predicts nucleotides 1 to 60 of SEQ ID NO: 3 encode a signal peptide. In another aspect, the mature polypeptide coding sequence is nucleotides 1 to 1782 of SEQ ID NO: 3 or the cDNA sequence thereof. In another aspect, the mature polypeptide coding sequence is nucleotides 112 to 1769 of SEQ ID NO: 5 or the cDNA sequence thereof based on the SignalP program that predicts nucleotides 1 to 57 of SEQ ID NO: 5 encode a signal peptide. In another aspect, the mature polypeptide coding sequence is nucleotides 1 to 1769 of SEQ ID NO: 5 or the cDNA sequence thereof. In another aspect, the mature polypeptide coding sequence is nucleotides 109 to 1743 of SEQ ID NO: 7 or the cDNA sequence thereof based on the SignalP program that predicts nucleotides 1 to 57 of SEQ ID NO: 7 encode a signal peptide. In another aspect, the mature polypeptide coding sequence is nucleotides 1 to 1743 of SEQ ID NO: 7 or the cDNA sequence thereof.

Catalytic domain: The term "catalytic domain" means the portion of an enzyme containing the catalytic machinery of the enzyme.

Cellulose binding domain: The term "cellulose binding domain" means the portion of an enzyme that mediates binding of the enzyme to amorphous regions of a cellulose substrate. The cellulose binding domain (CBD) is found either at the N-terminal or at the C-terminal extremity of an enzyme. A CBD is also referred to as a cellulose binding module or CBM. In one embodiment the CBM is amino acids 22 to 56 of SEQ ID NO: 2. In one embodiment the CBM is amino acids 21 to 57 of SEQ ID NO: 4. In one embodiment the CBM is amino acids 20 to 53 of SEQ ID NO: 6. In one embodiment the CBM is amino acids 20 to 53 of SEQ ID NO: 8. The CBM is separated from the catalytic domain by a linker sequence. The linker is in one embodiment amino acids 57 to 91 of SEQ ID NO: 2. The linker is in one embodiment amino acids 58 to 72 of SEQ ID NO: 4. The linker is in one embodiment amino acids 54 to 66 of SEQ ID NO: 6. The linker is in one embodiment amino acids 54 to 66 of SEQ ID NO: 8.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight Aspergillus oryzae beta-glucosidase (recombinantly produced in Aspergillus oryzae according to WO 02/095014) or 2-3% of total protein weight Aspergillus fumigatus beta-glucosidase (recombinantly produced in Aspergillus oryzae as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having endoglucanase activity. In one aspect, a subsequence contains at least 900 nucleotides, e.g., at least 1000 nucleotides or at least 1100 nucleotides of SEQ ID NO: 1, SEQ ID NO: 3, SEQ ID NO: 5, or SEQ ID NO: 7.

Variant: The term "variant" means a polypeptide having endoglucanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Endoglucanase Activity

In an embodiment, the present invention relates to isolated polypeptides having a sequence identity to the mature polypeptide of SEQ ID NO: 2 of at least 78%, e.g., at least 79%, at least 80%, at least 83%, at least 85%, at least 87%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 4 of at least 94%, e.g., at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 6 of at least 76%, e.g., at least 77%, at least 78%, at least 79%, at least 80%, at least 81%, at least 83%, at least 85%, at least 87%, at least 90%, at least 91%, at least 92%, at least 93%, at least 94%, at least 95%, at least 96%, at least 97%, at least 98%, at least 99%, or 100%, which have endoglucanase activity. In an embodiment, the present invention relates to isolated polypeptides having a sequence identity to the mature polypeptide of SEQ ID NO: 8 of at least 81%, e.g., at least 82%, at least 83%, at least 85%, at least 87%, at least 90%, at least 91%, at least 92%, at least 93%, at least 94%, at least 95%, at least 96%, at least 97%, at least 98%, at least 99%, or 100%, which have endoglucanase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, SEQ ID NO: 6, or SEQ ID NO: 8.

A polypeptide of the present invention preferably comprises or consists of the amino acid sequence of SEQ ID NO: 2, SEQ ID NO: 4, SEQ ID NO: 6, or SEQ ID NO: 8 or an allelic variant thereof; or is a fragment thereof having endoglucanase activity. In another aspect, the polypeptide comprises or consists of the mature polypeptide of SEQ ID NO: 2, SEQ ID NO: 4, SEQ ID NO: 6, or SEQ ID NO: 8. In another aspect, the polypeptide comprises or consists of amino acids 22 to 419 of SEQ ID NO: 2, amino acids 21 to 386 of SEQ ID NO: 4, amino acids 20 to 378 of SEQ ID NO: 6, or amino acids 20 to 378 of SEQ ID NO: 8.

In another embodiment, the present invention relates to an isolated polypeptide having endoglucanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, or SEQ ID NO: 7, or a subsequence thereof, as well as the polypeptide of SEQ ID NO: 2, SEQ ID NO: 4, SEQ ID NO: 6, or SEQ ID NO: 8, or a fragment thereof, may be used to design nucleic acid probes to identify and clone DNA encoding polypeptides having endoglucanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, or SEQ ID NO: 7 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, or SEQ ID NO: 7; (ii) the mature polypeptide coding sequence of SEQ ID NO: 1, SEQ ID NO: 3, SEQ ID NO: 5, or SEQ ID NO: 7; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, or SEQ ID NO: 8; the mature polypeptide thereof; or a fragment thereof. In another aspect, the nucleic acid probe is SEQ ID NO: 1, SEQ ID NO: 3, SEQ ID NO: 5, or SEQ ID NO: 7; or the cDNA sequence thereof.

In another embodiment, the present invention relates to an isolated polypeptide having endoglucanase activity encoded by a polynucleotide having a sequence identity to the mature polypeptide coding sequence of SEQ ID NO: 1, SEQ ID NO: 3, SEQ ID NO: 5, or SEQ ID NO: 7, or the cDNA sequence thereof, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, or SEQ ID NO: 8 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for endoglucanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Endoglucanase Activity

A polypeptide having endoglucanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Trametes* polypeptide.

In another aspect, the polypeptide is a *Trametes versicolor* polypeptide, e.g., a polypeptide obtained from *Trametes versicolor* Strain NN055586, or in another aspect the polypeptide is a polypeptide from a species related to *Trametes versicolor*, for example from another *Trametes* species.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

The present invention also relates to isolated polypeptides comprising a catalytic domain selected from the group consisting of:

(a) a catalytic domain having at least 60% sequence identity to the catalytic domain of SEQ ID NO: 2 (for example, amino acids 92 to 419 of SEQ ID NO: 2), SEQ ID NO: 4 (for example, amino acids 73 to 386 of SEQ ID NO: 4), SEQ ID NO: 6 (for example, amino acids 67 to 378 of SEQ ID NO: 6), or SEQ ID NO: 8 (for example, amino acids 67 to 378 of SEQ ID NO: 8);

(b) a catalytic domain encoded by a polynucleotide having at least 60% sequence identity to the catalytic domain coding sequence of SEQ ID NO: 1 (for example, nucleotides 459-564, 621-838, 896-993, 1050-1133, 1184-1345, 1410-1585, and 1639-1778 of SEQ ID NO: 1), SEQ ID NO: 3 (for example, nucleotides 334-459, 532-700, 760-808, 862-872, 931-956, 1019-1093, 1156-1312, 1384-1640, and 1711-1782 of SEQ ID NO: 3), SEQ ID NO: 5 (for example, nucleotides 361-408, 463-556, 613-618, 669-909, 975-1192, 1245-1297, 1362-1471, 1540-1688, and 1753-1769 of SEQ ID NO: 5), or SEQ ID NO: 7 (for example, nucleotides 355-402, 457-550, 607-612, 666-906, 969-1186, 1239-1291, 1353-1462, 1520-1668, and 1727-1743 of SEQ ID NO: 7);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, or SEQ ID NO: 8; and (d) a fragment of a catalytic domain of (a), (b), or (c), which has endoglucanase activity.

The catalytic domain preferably has a degree of sequence identity to the catalytic domain of SEQ ID NO: 2, SEQ ID NO: 4, SEQ ID NO: 6, or SEQ ID NO: 8 of at least 60%, e.g. at least 70%, at least 75%, at least 80%, at least 85%, at least 90%, at least 91%, at least 92%, at least 95%, at least 96%, at least 97%, at least 98%, at least 99%, or 100%. In an aspect, the catalytic domain comprises an amino acid sequence that differs by ten amino acids, e.g., by five amino acids, by four amino acids, by three amino acids, by two amino acids, and by one amino acid from the catalytic domain of SEQ ID NO: 2, SEQ ID NO: 4, SEQ ID NO: 6, or SEQ ID NO: 8.

The catalytic domain preferably comprises or consists of the catalytic domain of SEQ ID NO: 2 or an allelic variant thereof; or is a fragment thereof having endoglucanase activity. In another preferred aspect, the catalytic domain comprises or consists of amino acids 92 to 419 of SEQ ID NO: 2.

The catalytic domain preferably comprises or consists of the catalytic domain of SEQ ID NO: 4 or an allelic variant thereof; or is a fragment thereof having endoglucanase activity. In another preferred aspect, the catalytic domain comprises or consists of amino acids 73 to 386 of SEQ ID NO: 4.

The catalytic domain preferably comprises or consists of the catalytic domain of SEQ ID NO: 6 or an allelic variant thereof; or is a fragment thereof having endoglucanase activity. In another preferred aspect, the catalytic domain comprises or consists of amino acids 67 to 378 of SEQ ID NO: 6.

The catalytic domain preferably comprises or consists of the catalytic domain of SEQ ID NO: 8 or an allelic variant thereof; or is a fragment thereof having endoglucanase activity. In another preferred aspect, the catalytic domain comprises or consists of amino acids 67 to 378 of SEQ ID NO: 8.

In an embodiment, the catalytic domain may be encoded by a polynucleotide that hybridizes under very low stringency conditions, low stringency conditions, medium stringency conditions, medium-high stringency conditions, high stringency conditions, and very high stringency conditions (as defined above) with (i) the catalytic domain coding sequence of SEQ ID NO: 1, SEQ ID NO: 3, SEQ ID NO: 5, or SEQ ID NO: 7, (ii) the cDNA sequence contained in the catalytic domain coding sequence of SEQ ID NO: 1, SEQ ID NO: 3, SEQ ID NO: 5, or SEQ ID NO: 7, or (iii) the full-length complementary strand of (i) or (ii) (J. Sambrook et al., 1989, supra).

The catalytic domain may be encoded by a polynucleotide having a degree of sequence identity to the catalytic domain coding sequence of SEQ ID NO: 1, SEQ ID NO: 3, SEQ ID NO: 5, or SEQ ID NO: 7 of at least 60%, e.g. at least 70%, at least 75%, at least 80%, at least 85%, at least 90%, at least 91%, at least 92%, at least 95%, at least 96%, at least 97%, at least 98%, at least 99%, or 100%, which encode a polypeptide having endoglucanase activity.

In one aspect, the polynucleotide encoding the catalytic domain comprises or consists of nucleotides 459 to 1778 of SEQ ID NO: 1 or the cDNA sequence thereof. In particular the polynucleotide encoding the catalytic domain comprises or consists of nucleotides 459-564, 621-838, 896-993, 1050-1133, 1184-1345, 1410-1585, and 1639-1778 of SEQ ID NO: 1.

In one aspect, the polynucleotide encoding the catalytic domain comprises or consists of nucleotides 334 to 1782 of SEQ ID NO: 3 or the cDNA sequence thereof. In particular the polynucleotide encoding the catalytic domain comprises or consists of nucleotides 334-459, 532-700, 760-808, 862-872, 931-956, 1019-1093, 1156-1312, 1384-1640, and 1711-1782 of SEQ ID NO: 3.

In one aspect, the polynucleotide encoding the catalytic domain comprises or consists of nucleotides 361 to 1769 of SEQ ID NO: 5 or the cDNA sequence thereof. In particular the polynucleotide encoding the catalytic domain comprises or consists of nucleotides 361-408, 463-556, 613-618, 669-909, 975-1192, 1245-1297, 1362-1471, 1540-1688, and 1753-1769 of SEQ ID NO: 5.

In one aspect, the polynucleotide encoding the catalytic domain comprises or consists of nucleotides 355 to 1743 of SEQ ID NO: 7 or the cDNA sequence thereof. In particular the polynucleotide encoding the catalytic domain comprises or consists of nucleotides 355-402, 457-550, 607-612, 666-906, 969-1186, 1239-1291, 1353-1462, 1520-1668, and 1727-1743 of SEQ ID NO: 7.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trametes*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, or SEQ ID NO: 7, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80:

21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae*

TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis,*

*Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Trametes* cell. In a more preferred aspect, the cell is a *Trametes versicolor* cell. In a most preferred aspect, the cell is *Trametes versicolor* Strain NN055586.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, Nature 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following processes for using the polypeptides having endoglucanase activity, or compositions thereof.

The present invention also relates to processes for degrading a cellulosic material, comprising: treating the cellulosic material with an enzyme composition in the presence of a polypeptide having endoglucanase activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having endoglucanase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having endoglucanase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza et al., 2003, Optimal control in fed-batch reactor for the cellobiose hydrolysis, *Acta Scientiarum. Technology* 25: 33-38; Gusakov and Sinitsyn, 1985, Kinetics of the enzymatic hydrolysis of cellulose:

1. A mathematical model for a batch reactor process, *Enz. Microb. Technol.* 7: 346-352), an attrition reactor (Ryu et al., 1983, Bioconversion of waste cellulose by using an attrition bioreactor, *Biotechnol. Bioeng.* 25: 53-65), or a reactor with intensive stirring induced by an electromagnetic field (Gusakov et al., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having endoglucanase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having endoglucanase activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having endoglucanase activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having endoglucanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLIC™ CTec2 (Novozymes A/S), CELLUCLAST™ (Novozymes A/S), NOVOZYM™ (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, Gene 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydralase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7, 8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, ord about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8x212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number a1cc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8x211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C.*

*sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae*; *Clostridium*, such as *C. acetobutylicum, C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus, K. lactis, K thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka et al., 1997, Studies on hydrogen production by continuous culture system of hydrogen-producing anaerobic bacteria, *Water Science and Technology* 36 (6-7): 41-47; and Gunaseelan, 1997, Anaerobic digestion of biomass for methane production: A review, *Biomass and Bioenergy* 13(1-2): 83-114, 1997.

In another preferred aspect, the fermentation product is isoprene.

In another preferred aspect, the fermentation product is a ketone. It will be understood that the term "ketone" encompasses a substance that contains one or more ketone moieties.

In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 21 of SEQ ID NO: 2, amino acids 1 to 20 of SEQ ID NO: 4, amino acids 1 to 19 of SEQ ID NO: 6, or amino acids 1 to 19 of SEQ ID NO: 8. The polynucleotide may further comprise a gene encoding a protein, which is operably linked to the signal peptide. The protein is preferably foreign to the signal peptide. In one aspect, the polynucleotide encoding the signal peptide is nucleotides 1 to 63 of SEQ ID NO: 1. In another aspect, the polynucleotide encoding the signal peptide is nucleotides 1 to 60 of SEQ ID NO: 3. In another aspect, the polynucleotide encoding the signal peptide is nucleotides 1 to 57 of SEQ ID NO: 5. In another aspect, the polynucleotide encoding the signal peptide is nucleotides 1 to 57 of SEQ ID NO: 7.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide, which has at least 98% sequence identity to the sequence of amino acids 22-419 of SEQ ID NO: 2 or is a fragment of the sequence of amino acids 22-419 of SEQ ID NO: 2, wherein the polypeptide has endoglucanase activity.

2. The polypeptide of claim 1, having at least 98% sequence identity to the sequence of amino acids 22-419 of SEQ ID NO: 2.

3. The polypeptide of claim 1, having at least 99% sequence identity to the sequence of amino acids 22-419 of SEQ ID NO: 2.

4. The polypeptide of claim 1, which is a variant of the sequence of amino acids 22-419 of SEQ ID NO: 2, comprising a substitution, deletion, and/or insertion of one or more amino acids.

5. The polypeptide of claim 1, comprising the sequence of amino acids 22-419 of SEQ ID NO: 2.

6. The polypeptide of claim 1, which is encoded by a polynucleotide that hybridizes with the mature polypeptide coding sequence of SEQ ID NO: 1 or the cDNA sequence thereof under high stringency conditions.

7. The polypeptide of claim 1, which is a fragment of the sequence of amino acids 22-419 of SEQ ID NO: 2.

8. The polypeptide of claim 1, further comprising a cellulose binding domain.

9. A composition comprising a polypeptide of claim 1 and one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

10. A process for degrading a cellulosic material, comprising: treating the cellulosic material with a polypeptide of claim 1, a cellobiohydrolase, a beta-glucosidase, and a GH61 polypeptide having cellulolytic enhancing activity.

11. A process for producing a fermentation product, comprising:
  (a) saccharifying a cellulosic material with a polypeptide of claim 1, a cellobiohydrolase, a beta-glucosidase, and a GH61 polypeptide having cellulolytic enhancing activity; and
  (b) fermenting the saccharified cellulosic material with one or more fermenting microorganisms to produce the fermentation product.

12. The process of claim 11, further comprising recovering the fermentation product.

13. An isolated polypeptide comprising a catalytic domain, which has at least 99% sequence identity to the sequence of amino acids 92-419 of SEQ ID NO: 2 or is a fragment of the sequence of amino acids 92-419 of SEQ ID NO: 2, wherein the catalytic domain has endoglucanase activity.

14. The polypeptide of claim 13, further comprising a cellulose binding domain.

15. A composition comprising the polypeptide of claim 13 and one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

16. A process for degrading a cellulosic material, comprising: treating the cellulosic material with a polypeptide of claim 13, a cellobiohydrolase, a beta-glucosidase, and a GH61 polypeptide having cellulolytic enhancing activity.

17. A process for producing a fermentation product, comprising:
  (a) saccharifying a cellulosic material with a polypeptide of claim 13, a cellobiohydrolase, a beta-glucosidase, and a GH61 polypeptide having cellulolytic enhancing activity; and
  (b) fermenting the saccharified cellulosic material with one or more fermenting microorganisms to produce the fermentation product.

18. The process of claim 17, further comprising recovering the fermentation product.

\* \* \* \* \*